US011286227B2

(12) United States Patent
Yamashita et al.

(10) Patent No.: US 11,286,227 B2
(45) Date of Patent: Mar. 29, 2022

(54) PROCESSES FOR PREPARING 2-ISOPROPENYL-5-METHYL-4-HEXENOIC ACID, 2-ISOPROPENYL-5-METHYL-4-HEXEN-1-OL, AND A CARBOXYLATE ESTER THEREOF

(71) Applicant: Shin-Etsu Chemical Co., Ltd., Tokyo (JP)

(72) Inventors: Miyoshi Yamashita, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/234,872

(22) Filed: Apr. 20, 2021

(65) Prior Publication Data

US 2021/0323902 A1 Oct. 21, 2021

(30) Foreign Application Priority Data

Apr. 21, 2020 (JP) ............................ JP2020-075249

(51) Int. Cl.
*C07C 51/09* (2006.01)
*C07C 29/147* (2006.01)
*C07C 67/08* (2006.01)
*C07C 57/03* (2006.01)

(52) U.S. Cl.
CPC ............ *C07C 51/09* (2013.01); *C07C 29/147* (2013.01); *C07C 57/03* (2013.01); *C07C 67/08* (2013.01)

(58) Field of Classification Search
CPC ....... C07C 51/09; C07C 29/147; C07C 67/08; C07C 57/03
See application file for complete search history.

(56) References Cited

U.S. PATENT DOCUMENTS

2015/0119597 A1* 4/2015 Kinsho ................ C07C 67/333 560/129
2015/0119598 A1* 4/2015 Kinsho ................ C07C 51/353 560/205

FOREIGN PATENT DOCUMENTS

EP 2868651 A1 5/2015
JP 2015110553 A 6/2015

OTHER PUBLICATIONS

Extended European Search Report corresponding to European Patent Application No. 21169104.3 (5 pages) (dated Sep. 17, 2021).
Baudouy, René , et al., "Synthese diastereoselective d'une composante de la pheromone sexuelle de "l'ecaille rouge de californie" : l'acetate d'isopropenyl-6 methyl-3 decene-9 yle (3S, 6R)", Tetrahedron 44(2), 1988, 471-480.
Dragan, V. A. , et al., "Synthesis of the AI component of the red san jose scale sex pheromone", Bulletin of the Academy of Sciences of the USSR, Division of chemical science 38, 1989, pp. 1038-1041.
Gieselmann, M.J. , et al., "Responses of male California red scale to sex pheromone isomers", Journal of Insect Physiology 26(3), 1980, 179-182.
Kefalas, Panagiotis , et al., "Efficient Synthesis of the *Aonidiella aurantii* (Mask.) Sex Pheromone Component: (3S,6RS)-3Methyl6-(1-Methylethenyl)-9-decenyl Acetate", Synthesis 6, 1995, 644-646.
De Alfonso, Ignacio , et al., "Identification of the Sex Pheromone of the Mealybug *Dysmicoccus grassii* Leonardi", J. Agric. Food Chem. 60(48), 2012, 11959-11964.

(Continued)

*Primary Examiner* — Yate' K Cutliff
(74) *Attorney, Agent, or Firm* — Myers Bigel, P.A.

(57) ABSTRACT

The present invention provides a process for preparing 2-isopropenyl-5-methyl-4-hexenoic acid of the following formula (4), comprising steps of:

subjecting a Grignard reagent of the following general formula (1), wherein $R^1$ represents a linear, branched, or aromatic monovalent hydrocarbon group having 1 to 8 carbon atoms, and X represents a chlorine atom, a bromine atom, or an iodine atom, and 1,1,1,3,3,3-hexamethyldisilazane to a deprotonation reaction to form a 1,1,1,3,3,3-hexamethyldisilazane derivative; and subjecting 2-methyl-3-buten-2-yl 3-methyl-2-butenoate of the following formula (3) to a rearrangement reaction in the presence of the 1,1,1,3,3,3-hexamethyldisilazane derivative to form 2-isopropenyl-5-methyl-4-hexenoic acid (4).

$R^1MgX$ (1) + $(CH_3)_3Si-NH-Si(CH_3)_3$ → 1,1,1,3,3,3-Hexamethyldisilazane derivative (3) —1,1,1,3,3,3-Hexamethyldisilazane derivative→ (4)

3 Claims, No Drawings

(56) References Cited

OTHER PUBLICATIONS

Hinkens, Diane M., et al., “Identification and synthesis of the sex pheromone of the vine mealybug, *Pianococcus ficus*”, Tetrahedron Letters 42(9), 2001, 1619-1621.
Ho, Hsiao-Yung , et al., “Identification and Synthesis of the Sex Pheromone of the Madeira Mealybug, *Phenacoccus madeirensis* Green”, Journal of Chemical Ecology 35, 2009, 724-732.
Matsui, Masanao , et al., “New Attempt at the Synthesis of Lavandulol by a Claisen Type Rearrangement”, Agro. Biol. Chem. 32(10), 1968, 1246-1249.
Zhang, Aijun , et al., “Sex Pheromone of the Female Pink Hibiscus Mealybug, *Maconellicoccus hirsutus* (Green) (Homoptera: Pseudococcidae): Biological Activity Evaluation”, Environmental Entomology 34(2), 2005, 264-270.

* cited by examiner

PROCESSES FOR PREPARING 2-ISOPROPENYL-5-METHYL-4-HEXENOIC ACID, 2-ISOPROPENYL-5-METHYL-4-HEXEN-1-OL, AND A CARBOXYLATE ESTER THEREOF

CROSS-REFERENCE TO RELATED APPLICATION

This U.S. nonprovisional application claims priority to Japanese Application No. 2020-075249 filed Apr. 21, 2020, the entire contents of which is incorporated herein by reference.

TECHNICAL FIELD

The present invention relates to processes for preparing 2-isopropenyl-5-methyl-4-hexenoic acid, 2-isopropenyl-5-methyl-4-hexen-1-ol, and a carboxylate ester thereof.

BACKGROUND ART

2-Isopropenyl-5-methyl-4-hexen-1-ol (generic name: lavandulol) is known as a flavor ingredient of lavender oil and lavandin oil and widely used as a perfume in cosmetics and fragrances. Natural essential oils contain an (R)-optical isomer thereof having an herbal citrus flavor. Meanwhile, an (S)-optical isomer thereof has only weak odor. Therefore, a mixture of the optical isomers is chemically synthesized at less costs.

2-Isopropenyl-5-methyl-4-hexen-1-yl carboxylate is reported to be a component of sex pheromone of mealybugs, for example, vine mealybug (scientific name: *Planococcus ficus*) (Non-Patent Literature 1 listed below), banana mealybug (scientific name: *Dysmicoccus grassii*) (Non-Patent Literature 2 listed below), pink hibiscus mealybug (scientific name: *Maconelhcoccus hirsutus*) (Non-Patent Literature 3 listed below), and Madeira mealybug (scientific name: *Phenacoccus madeirensis*) (Non-Patent Literature 4 listed below).

Recently, owing to concerns about influence of insecticides on the environment and human health, development of new pest control techniques is desired, such as mating disruption and/or mass trapping using sex pheromone substances. Such technological development requires industrial and inexpensive preparation of sex pheromone components in a large scale. The aforesaid 2-isopropenyl-5-methyl-4-hexen-1-yl carboxylate which is a sex pheromone component of mealybugs has optical activity. A case is known where when one of the optical isomers of the compound is a naturally occurring type, the other optical isomer, which is a non-naturally occurring type, may not adversely affect a function of the sex pheromone component. In such a case, it is advantageous in view of commercialization to prepare a mixture of optical isomers with less costs.

2-Isopropenyl-5-methyl-4-hexenoic acid is a useful precursor of for 2-isopropenyl-5-methyl-4-hexen-1-ol. Reduction of a carboxyl moiety of this precursor into an alcohol moiety with a reducing agent easily gives 2-isopropenyl-5-methyl-4-hexen-1-ol. However, 2-isopropenyl-5-methyl-4-hexenoic acid is known to easily undergo positional isomerization of the carbon-carbon double bond between the β- and γ-positions into the carbonyl-conjugated double bond between the α- and β-positions in a basic condition. This positional isomerization results in by-production of 2-isopropylidene-5-methyl-4-hexenoic acid, which is a regioisomer of 2-isopropenyl-5-methyl-4-hexenoic acid. It is difficult to separate this regioisomer industrially. Then, when the carboxyl moiety of 2-isopropenyl-5-methyl-4-hexenoic acid is reduced, the carboxyl moiety of 2-isopropylidene-5-methyl-4-hexenoic acid is also reduced at the same time. This results in a mixture of 2-isopropenyl-5-methyl-4-hexen-1-ol, which is a reduction product of 2-isopropenyl-5-methyl-4-hexenoic acid, and 2-isopropylidene-5-methyl-4-hexen-1-ol (generic name: isolavandulol), which is a reduction product of 2-isopropylidene-5-methyl-4-hexenoic acid.

This intermixed 2-isopropylidene-5-methyl-4-hexen-1-ol may cause an influence to the native flavor of 2-isopropenyl-5-methyl-4-hexen-1-ol used as a perfume, and also an adverse effect of inhibiting the function of 2-isopropenyl-5-methyl-4-hexen-1-yl carboxylate as a sex pheromone component of mealybugs. Therefore, contamination with the regioisomer is required to be minimized.

A process for preparing 2-isopropenyl-5-methyl-4-hexenoic acid is known wherein 2-methyl-3-buten-2-yl 3-methyl-2-butenoate is converted into its dienolate using a base and then the dienolate is subjected to a rearrangement reaction. Sodium hydride is used as a base, as reported in the following Patent Literature 1 and Non-Patent Literature 5. Lithium bis(trimethylsilyl)amide is used as a base, as reported in the following Patent Literature 1.

LIST OF THE PRIOR LITERATURES

[Patent Literature 1] Japanese Patent Application Laid-Open No. 2015-110553

[Non-Patent Literature 1] Diane M. Hinkens et. al., Tetrahedron Letters 42 (2001) 1619-1621.

[Non-Patent Literature 2] I. d. Dealfonso et. al., J. Agric. Food Chem. 2012, 60, 11959-11964.

[Non-Patent Literature 3] A. Zhang et. al., Environ. Entmol. 34, 2005, 264-270.

[Non-Patent Literature 4] H.-Y. Ho, J. Chem. Ecol., (2009) 35, 724-732.

[Non-Patent Literature 5] M. Matsui et. al., Agr. Biol. Chem., 1968, 32, 1246-1249.

Problems to be Solved by the Invention

The methods described in Patent Literature 1 and Non-Patent Literature 5, in which sodium hydride is used as a base, generate a large amount of a by-product, 2-isopropylidene-5-methyl-4-hexenoic acid, which is a regioisomer of 2-isopropenyl-5-methyl-4-hexenoic acid. The method described in Patent Literature 1, in which lithium bis(trimethylsilyl)amide is used as a base, requires the reaction to be carried out in a ultralow temperature. If the method is carried out in an industrially practical reaction temperature, a conversion is low to give a low yield, and the regioisomer is by-produced. Thus, the prior technologies fail to offer any industrial and economical, large-scale preparation of the envisaged compound.

SUMMARY OF THE INVENTION

The present invention has been made in these circumstances, and aims to overcome the aforesaid problems of the prior art to provide processes for industrially and economically preparing 2-isopropenyl-5-methyl-4-hexenoic acid, 2-isopropenyl-5-methyl-4-hexen-1-ol, and a carboxylate ester thereof, that is, 2-isopropenyl-5-methyl-4-hexen-1-yl carboxylate.

As a result of the intensive researches, the present inventors have found that 2-isopropenyl-5-methyl-4-hexenoic acid is prepared in a favorable yield and quality in industrially practical reaction conditions while suppressing or eliminating decrease in a conversion and by-production of its regioisomer, by subjecting a predetermined Grignard reagent and 1,1,1,3,3,3-hexamethyldisilazane to a deprotonation reaction to form a 1,1,1,3,3,3-hexamethyldisilazane derivative and subjecting 2-methyl-3-buten-2-yl 3-methyl-2-butenoate to a rearrangement reaction in the presence of the 1,1,1,3,3,3-hexamethyldisilazane derivative. Thus, the present invention has been invented.

The present inventors have also found that 2-isopropenyl-5-methyl-4-hexenoic acid thus obtained may be used to efficiently and industrially prepare 2-isopropenyl-5-methyl-4-hexen-1-ol and a 2-isopropenyl-5-methyl-4-hexen-1-yl carboxylate, and thus have completed the present invention.

One aspect of the present invention provides a process for preparing 2-isopropenyl-5-methyl-4-hexenoic acid of the following formula (4):

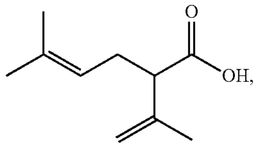

(4)

the process comprising steps of:

subjecting a Grignard reagent of the following general formula (1):

$R^1MgX$ (1)

wherein $R^1$ represents a linear, branched, or aromatic monovalent hydrocarbon group having 1 to 8 carbon atoms, and X represents a chlorine atom, a bromine atom, or an iodine atom, and 1,1,1,3,3,3-hexamethyldisilazane to a deprotonation reaction to form a 1,1,1,3,3,3-hexamethyldisilazane derivative; and subjecting 2-methyl-3-buten-2-yl 3-methyl-2-butenoate of the following formula (3):

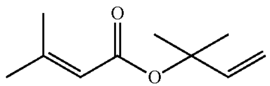

(3)

to a rearrangement reaction in the presence of the 1,1,1,3,3,3-hexamethyldisilazane derivative to form 2-isopropenyl-5-methyl-4-hexenoic acid (4).

Another aspect of the present invention provides a process for preparing 2-isopropenyl-5-methyl-4-hexen-1-ol of the following formula (5):

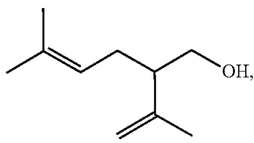

(5)

the process comprising a step of reducing 2-isopropenyl-5-methyl-4-hexenoic acid (4) thus prepared to form 2-isopropenyl-5-methyl-4-hexen-1-ol (5).

Another aspect of the present invention further provides a process for preparing a 2-isopropenyl-5-methyl-4-hexen-1-yl carboxylate of the following general formula (6):

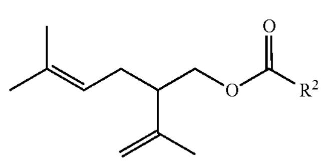

(6)

wherein $R^2$ represents a linear or branched monovalent hydrocarbon group having 1 to 6 carbon atoms, the process comprising esterifying 2-isopropenyl-5-methyl-4-hexen-1-ol (5) thus prepared to form 2-isopropenyl-5-methyl-4-hexen-1-yl carboxylate (6).

The present invention makes it possible to efficiently prepare 2-isopropenyl-5-methyl-4-hexenoic acid in high purity in industrially practical reaction conditions without decrease in a conversion and/or by-production of a regioisomer.

The present invention also makes it possible to industrially and economically prepare 2-isopropenyl-5-methyl-4-hexen-1-ol, which is known as a perfume, and a 2-isopropenyl-5-methyl-4-hexen-1-yl carboxylate, which is a sex pheromone of mealybugs, starting from 2-isopropenyl-5-methyl-4-hexenoic acid.

DETAILED DESCRIPTION OF THE PREFERRED EMBODIMENTS

Embodiments of the present invention will be explained below in detail. It should be understood that the present invention is not limited to or by the following embodiments.

First, the step of subjecting a Grignard reagent of the following general formula (1) (hereinafter referred to also as "Grignard reagent (1)") and 1,1,1,3,3,3-hexamethyldisilazane to a deprotonation reaction to form a 1,1,1,3,3,3-hexamethyldisilazane derivative (2) will be described below.

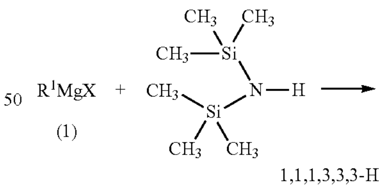

1,1,1,3,3,3-Hexamethyldisilazane derivative (2)

$R^1$ in the general formula (1) represents a linear, branched, or aromatic monovalent hydrocarbon group having 1 to 8, preferably 1 to 3 carbon atoms.

Examples of the monovalent hydrocarbon group, $R^1$, include linear monovalent hydrocarbon groups such as a methyl group, an ethyl group, a 1-propyl group, and a 1-pentyl group; branched monovalent hydrocarbon groups such as a 2-propyl group, a 2-butyl group, a 2-hexyl group, a 2-methylbutyl group, and a 1,1-dimethylethyl group; and aromatic monovalent hydrocarbon groups such as a phenyl group and a p-tolyl group.

X in the general formula (1) represents a chlorine atom, a bromine atom, or an iodine atom, preferably a chlorine atom.

Examples of the Grignard reagent (1) include an organomagnesium chloride, an organomagnesium bromide, and an organomagnesium iodide.

Examples of the organomagnesium chloride include linear organomagnesium chlorides such as methylmagnesium chloride, ethylmagnesium chloride, 1-propylmagnesium chloride, and 1-pentylmagnesium chloride; branched organomagnesium chlorides such as 2-propylmagnesium chloride, 2-butylmagnesium chloride, 2-hexylmagnesium chloride, 2-methylbutylmagnesium chloride, and 1,1-dimethylethylmagnesium chloride; and aromatic organomagnesium chlorides such as phenylmagnesium chloride and p-tolylmagnesium chloride.

Examples of the organomagnesium bromide include linear organomagnesium bromides such as methylmagnesium bromide, ethylmagnesium bromide, 1-propylmagnesium bromide, and 1-pentylmagnesium bromide; branched organomagnesium bromides such as 2-propylmagnesium bromide, 2-butylmagnesium bromide, 2-hexylmagnesium bromide, 2-methylbutylmagnesium bromide, and 1,1-dimethylethylmagnesium bromide; and aromatic organomagnesium bromides such as phenylmagnesium bromide and p-tolylmagnesium bromide.

Examples of the organomagnesium iodide include linear organomagnesium iodides such as methylmagnesium iodide, ethylmagnesium iodide, 1-propylmagnesium iodide, and 1-pentylmagnesium iodide; branched organomagnesium iodides such as 2-propylmagnesium iodide, 2-butylmagnesium iodide, 2-hexylmagnesium iodide, 2-methylbutylmagnesium iodide, and 1,1-dimethylethylmagnesium iodide; and aromatic organomagnesium iodides such as phenylmagnesium iodide and p-tolylmagnesium iodide.

The Grignard reagent (1) may be used alone or in combination thereof, if necessary.

Next, the preparation of the Grignard reagent (1) will be explained. The Grignard reagent (1) may be a commercially available one or may be prepared by reacting an organohalide with metal magnesium in a solvent in any known method.

Examples of the organohalide include organochlorides, organobromides, and organoiodides.

Examples of the organochlorides include linear organochlorides such as methyl chloride, ethyl chloride, 1-propyl chloride, and 1-pentyl chloride; branched organochlorides such as 2-propyl chloride, 2-butyl chloride, 2-hexyl chloride, 2-methylbutyl chloride, and 1,1-dimethylethyl chloride; and aromatic organochlorides such as phenyl chloride and p-tolyl chloride.

Examples of the organobromides include linear organobromides such as methyl bromide, ethyl bromide, 1-propyl bromide, and 1-pentyl bromide; branched organobromides such as 2-propyl bromide, 2-butyl bromide, 2-hexyl bromide, 2-methylbutyl bromide, and 1,1-dimethylethyl bromide; and aromatic organobromides such as phenyl bromide and p-tolyl bromide.

Examples of the organoiodides include linear organoiodides such as methyl iodide, ethyl iodide, 1-propyl iodide, and 1-pentyl iodide; branched organoiodides such as 2-propyl iodide, 2-butyl iodide, 2-hexyl iodide, 2-methylbutyl iodide, and 1,1-dimethylethyl iodide; and aromatic organoiodides such as phenyl iodide and p-tolyl iodide.

A solvent to be used in the preparation of Grignard reagent (1) is typically ether solvents such as diethyl ether, methyl t-butyl ether, cyclopentyl methyl ether, tetrahydrofuran, 2-methyltetrahydrofuran, 1,4-dioxane, and 4-methyltetrahydropyran.

The solvent may be used alone or in combination thereof, if necessary. The solvent may be used for adjusting a concentration and/or a reaction temperature insofar as it does not adversely affect the preparation of Grignard reagent (1). The solvent may be commercially available one.

An amount of the solvent is preferably from 50 g to 1,000 g, more preferably from 100 g to 500 g, per mol of the organohalide in view of the economy and reactivity.

A reaction temperature in the preparation of the Grignard reagent (1) is preferably from 20° C. to 120° C., more preferably from 40° C. to 80° C. in view of the reactivity and easy control of a reaction rate.

An amount of the metal magnesium to be used in the preparation of the Grignard reagent (1) may be set arbitrarily. Typically, the metal magnesium is used in an excessive amount relative to the organohalide. When the organohalide has a low boiling point, the organohalide is used in an excessive amount relative to the metal magnesium, and the excess organohalide may be removed in a gaseous form or distilled off in a liquid form.

Next, the step of subjecting the Grignard reagent (1) and 1,1,1,3,3,3-hexamethyldisilazane to a deprotonation reaction will be explained below.

1,1,1,3,3,3-Hexamethyldisilazane is known also as bis(trimethylsilyl)amine.

The deprotonation reaction may be carried out in the presence of a solvent and, if necessary, under heating or cooling.

1,1,1,3,3,3-Hexamethyldisilazane may be a commercially available one or may be prepared in a known reaction of trimethylsilyl chloride with ammonia.

An amount of 1,1,1,3,3,3-hexamethyldisilazane to be used is preferably from 1.0 to 2.0 mol, more preferably from 1.05 to 1.25 mol, per mol of the Grignard reagent (1), in view of the reactivity and suppression of formation of impurities.

Examples of the solvent used in the deprotonation reaction include ether solvents such as diethyl ether, methyl t-butyl ether, cyclopentyl methyl ether, tetrahydrofuran, 2-methyltetrahydrofuran, 1,4-dioxane, and 4-methyltetrahydropyran; and hydrocarbon solvents such as pentane, hexane, heptane, cyclohexane, benzene, and toluene. In view of the reactivity or yield, tetrahydrofuran and diethyl ether are preferred. The solvent used in the preparation of the Grignard reagent (1) may be used as such in the deprotonation reaction.

The solvent to be used in the deprotonation reaction may be alone or in combination thereof, if necessary. The solvent may be commercially available one.

An amount of the solvent is preferably from 100 g to 1,000 g, more preferably from 250 g to 600 g, per mol of the Grignard reagent (1) in view of the reactivity and economy.

A reaction temperature of the deprotonation reaction is preferably from 0° C. to 120° C., more preferably from 20° C. to 50° C. in view of the reactivity and yield.

In the deprotonation reaction of 1,1,1,3,3,3-hexamethyldisilazane with the Grignard reagent (1), a 1,1,1,3,3,3-hexamethyldisilazane derivative is formed. The 1,1,1,3,3,3-hexamethyldisilazane derivative (2) thus prepared is theoretically presumed to be a halomagnesium bis(trimethylsilyl)amide of the following general formula (2A):

(2A)

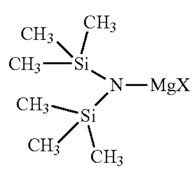

wherein X represents a chlorine atom, a bromine atom, or an iodine atom.

In the process according to the present invention, the reaction mixture after the deprotonation reaction may be used as such without being purified, as a base in the subsequent step (i.e., rearrangement reaction). In the following Examples 1 to 5 of the present invention, spectral data of the 1,1,1,3,3,3-hexamethyldisilazane derivative (2) produced in the deprotonation reaction are not particularly shown.

Next, the step of subjecting 2-methyl-3-buten-2-yl 3-methyl-2-butenoate of the following formula (3) to a rearrangement reaction in the presence of the 1,1,1,3,3,3-hexamethyldisilazane derivative (2) to form 2-isopropenyl-5-methyl-4-hexenoic acid of the following formula (4) will be explained below.

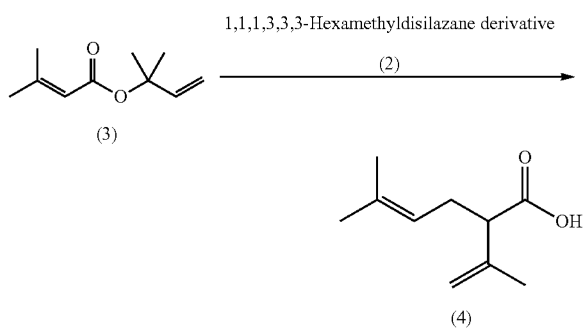

2-Methyl-3-buten-2-yl 3-methyl-2-butenoate (3) may be prepared in any known method. Specifically, examples of the known preparation methods are described in Non-Patent Literature 5, where 2-methyl-3-buten-2-ol is reacted with sodium hydride to form a sodium alkoxide which is then reacted with 3-methyl-2-butenoyl chloride. Alternatively, as described in the present Example, 3-methyl-2-butenoic acid is reacted with 2-methyl-3-buten-2-ol and p-toluenesulfonyl chloride or benzenesulfonyl chloride in the presence of pyridine.

The rearrangement reaction proceeds by reacting 2-methyl-3-buten-2-yl 3-methyl-2-butenoate (3) with the 1,1,1,3,3,3-hexamethyldisilazane derivative (2) as a base to form a dienolate. This rearrangement reaction may be carried out under heating or cooling, if necessary.

An amount of the 1,1,1,3,3,3-hexamethyldisilazane derivative (2) to be used is preferably from 1.05 mol to 1.5 mol, more preferably from 1.1 to 1.3 mol, per mol of 2-methyl-3-buten-2-yl 3-methyl-2-butenoate (3) in view of the reactivity and suppression of formation of impurities.

The solvent used in the rearrangement reaction is not particularly limited insofar as it does not adversely affect the reaction. Example of the solvent include ether solvents such as diethyl ether, methyl t-butyl ether, cyclopentyl methyl ether, tetrahydrofuran, 2-methyltetrahydrofuran, 1,4-dioxane, and 4-methyltetrahydropyran; and hydrocarbon solvents such as pentane, hexane, heptane, cyclohexane, benzene, and toluene. In view of the reactivity or yield, tetrahydrofuran and diethyl ether are preferred. The solvent used in the preparation of the Grignard reagent or the deprotonation reaction may be used as such.

A solvent may be used alone or in combination thereof, if necessary. The solvent may be commercially available one.

An amount of the solvent used is preferably from 100 g to 1,000 g, more preferably from 300 g to 700 g, per mol of the 2-methyl-3-buten-2-yl 3-methyl-2-butenoate (3), in view of the reactivity and economy.

A reaction temperature in the rearrangement reaction is preferably from 25° C. to 80° C., more preferably from 30° C. to 60° C. in view of the reactivity and yield.

2-Isopropenyl-5-methyl-4-hexenoic acid (4) may be isolated and purified in any purification method used in ordinary organic syntheses, such as distillation at a reduced pressure and/or various chromatography. In view of the industrial economy, distillation at a reduced pressure is preferred. When a target chemical compound has a sufficient purity, a crude product may be used as such without being purified, in a subsequent step.

Examples of 2-isopropenyl-5-methyl-4-hexenoic acid (4) obtained in the rearrangement reaction include (R)-2-isopropenyl-5-methyl-4-hexenoic acid, (S)-2-isopropenyl-5-methyl-4-hexenoic acid, and a racemate and a scalemic mixture thereof.

Next, the step of reducing the carboxyl moiety of 2-isopropenyl-5-methyl-4-hexenoic acid (4) thus prepared into an alcohol moiety to form 2-isopropenyl-5-methyl-4-hexen-1-ol of the following formula (5) will be explained below.

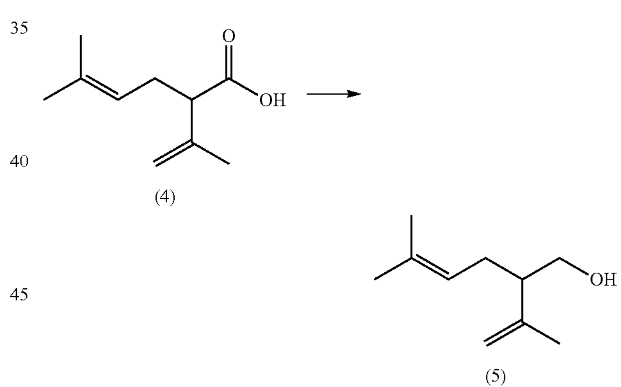

The reduction reaction may be carried out with a reducing agent and, if necessary, under heating or cooling.

The reducing agent is not particularly limited and may be any known reducing agent.

Examples of the reducing agent include hydrogen; boron compounds such as a borane, an alkylborane, a dialkylborane, and a bis(3-methyl-2-butyl)borane; metal hydrides such as a dialkylsilane, a trialkylsilane, an aluminum hydride, an alkylaluminum hydride, a dialkylaluminum hydride, sodium hydride, lithium hydride, potassium hydride, and calcium hydride; and metal hydride complexes such as sodium borohydride, lithium borohydride, potassium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-t-butoxyaluminum hydride, and sodium bis(2-methoxyethoxy)aluminum hydride. In view of the reactivity and/or yield, metal hydride complexes are preferred.

The reducing agent may be used alone or in combination thereof, if necessary. The reducing agent may be commercially available one.

The reduction reaction may be carried out otherwise after converting 2-isopropenyl-5-methyl-4-hexenoic acid (4) into an ester, an acid halide, an acid anhydride, or a mixed acid anhydride.

An amount of the reducing agent used in the reduction reaction may be set, depending on the reactivity of the reducing agent and/or the reaction mechanism, and is preferably from 0.2 mol to 10.0 mol, more preferably from 0.25 mol to 5.0 mol, per mol of 2-isopropenyl-5-methyl-4-hexenoic acid (4) in view of the reactivity and economy.

For example, an amount of lithium aluminum hydride is preferably from 0.75 mol to 3.0 mol, more preferably from 1.0 mol to 2.0 mol, per mol of 2-isopropenyl-5-methyl-4-hexenoic acid (4).

An amount of hydrogen atoms or hydride ions of the reducing agent is preferably from 0.2 mol to 40.0 mol, more preferably from 0.25 mol to 20.0 mol in view of the reactivity and economy. An amount of the hydrogen atoms or hydride ions used is decided by the kind of the reducing agent used and/or the amount thereof.

A solvent used in the reduction reaction is not particularly limited insofar as it does not adversely affect the reaction.

Examples of the solvent include water; hydrocarbon solvents such as hexane, heptane, octane, benzene, toluene, and xylene; ether solvents such as diethyl ether, dibutyl ether, cyclopentyl methyl ether, diethylene glycol diethyl ether, diethylene glycol dimethyl ether, tetrahydrofuran, and 1,4-dioxane; alcohol solvents such as methanol, ethanol, 1-propanol, and 2-propanol; nitrile solvents such as acetonitrile; ketone solvents such as acetone and methyl ethyl ketone; ester solvents such as methyl acetate, ethyl acetate, and n-butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The solvent may be commercially available one.

For example, when lithium aluminum hydride is used as a reducing agent, the solvent is preferably an ether solvent such as tetrahydrofuran, diethylene glycol diethyl ether, or 1,4-dioxane. A mixture of the ether solvent and the hydrocarbon solvent such as hexane, heptane, octane, benzene, toluene, or xylene may be also used.

A reaction temperature in the reduction reaction may be in a temperature range that does not adversely affect the reaction, and is preferably from −50° C. to 50° C., more preferably from −25° C. to 25° C., in view of a yield and suppression of formation of by-products. For example, when lithium aluminum hydride is used as the reducing agent, the reaction temperature is preferably from −10° C. to 35° C., more preferably from 0° C. to 30° C.

The obtained 2-isopropenyl-5-methyl-4-hexen-1-ol (5) may be isolated and purified in any purification method used in ordinary organic synthesis, such as distillation at a reduced pressure and/or various chromatography. In view of the industrial economy, distillation at a reduced pressure is preferred. When the target chemical compound has a sufficient purity, the crude product may be used as such without being purified, in a subsequent step.

Examples of the 2-isopropenyl-5-methyl-4-hexen-1-ol (5) obtained in the reduction reaction include (R)-2-isopropenyl-5-methyl-4-hexen-1-ol, (S)-2-isopropenyl-5-methyl-4-hexen-1-ol, and a racemate and a scalemic mixture thereof.

Next, the step of esterifying the alcohol compound, 2-isopropenyl-5-methyl-4-hexen-1-ol (5), to form a 2-isopropenyl-5-methyl-4-hexen-1-yl carboxylate of the following general formula (6) will be explained below.

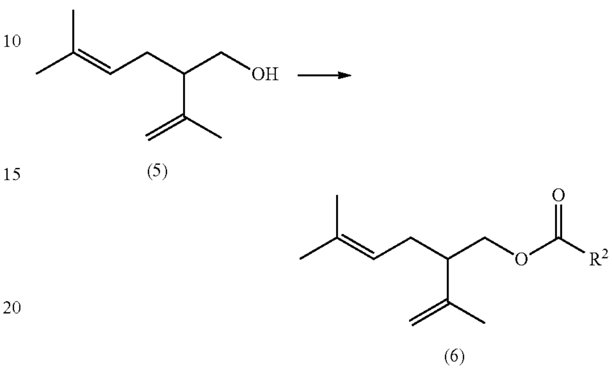

The aforesaid esterification step may be done in any known esterification method, such as (A) an acylation with an acylating agent, (B) a dehydration with a carboxylic acid, (C) a transesterification with a carboxylate ester, and (D) conversion of 2-isopropenyl-5-methyl-4-hexen-1-ol (5) into an alkylating agent, followed by acyloxylation with a carboxylic acid, but not limited to these. The aforesaid (A) to (D) will be explained below in detail.

(A) Acylation with an Acylating Agent

The acylation of 2-isopropenyl-5-methyl-4-hexen-1-ol (5) with an acylating agent may be carried out typically in the presence of a base or catalyst.

The acylating agent is represented by $R^2COCl$, $R^2COBr$, or $R^2COOCOR^2$, wherein $R^2$ represents a linear or branched monovalent hydrocarbon group having 1 to 6 carbon atoms.

Examples of $R^2$ include linear saturated hydrocarbon groups such as a methyl group, an ethyl group, a 1-propyl group, and a 1-butyl group; branched saturated hydrocarbon groups such as a 2-propyl group, a 2-methylpropyl group, a 2-butyl group, a 2-pentyl group, and a 1,1-dimethylethyl group; linear unsaturated hydrocarbon groups such as a 1-propenyl group, a 1-butenyl group, a 2-butenyl group, a 1-pentenyl group, and a 2-pentenyl group; and branched unsaturated hydrocarbon groups such as a 1-methylpropenyl group, a 2-methylpropenyl group, a 2-methylbutenyl group, and a 2-methyl-2-butenyl group.

Examples of the acylating agent include carbonyl chlorides, carbonyl bromides, and carboxylic anhydrides.

Examples of the carbonyl chlorides include linear saturated carbonyl chlorides such as acetyl chloride and propionyl chloride; branched saturated carbonyl chlorides such as 2-methylpropionyl chloride, 2-methylbutanoyl chloride, and 3-methylbutanoyl chloride; linear unsaturated carbonyl chlorides such as 2-butenoyl chloride and 2-pentenoyl chloride; and branched unsaturated carbonyl chlorides such as 2-methyl-2-butenoyl chloride and 3-methyl-2-butenoyl chloride.

Examples of the carbonyl bromides include linear saturated carbonyl bromides such as acetyl bromide and propionyl bromide; branched saturated carbonyl bromides such as 2-methylpropionyl bromide, 2-methylbutanoyl bromide, and 3-methylbutanoyl bromide; linear unsaturated carbonyl bromides such as 2-butenoyl bromide and 2-pentenoyl bromide; and branched unsaturated carbonyl bromides such as 2-methyl-2-butenoyl bromide and 3-methyl-2-butenoyl bromide.

Examples of the carboxylic anhydrides include linear saturated carboxylic anhydrides such as acetic anhydride and propionic anhydride; branched saturated carboxylic anhydrides such as 2-methylpropionic anhydride, 2-methylbutanoic anhydride, and 3-methylbutanoic anhydride; linear unsaturated carboxylic anhydrides such as 2-butenoic anhydride and 2-pentenoic anhydride; and branched unsaturated carboxylic anhydrides such as 2-methyl-2-butenoic anhydride and 3-methyl-2-butenoic anhydride.

An amount of the acylating agent used is preferably from 1.0 mol to 30.0 mol, more preferably from 1.0 mol to 5.0 mol, per mol of 2-isopropenyl-5-methyl-4-hexen-1-ol (5) in view of the economy.

Examples of the base used in the acylation include amines such as triethylamine, pyridine, N,N-dimethylaminopyridine, and N,N-dimethylaniline; organometallic compounds such as n-butyllithium, methyllithium, and phenyllithium; metal hydroxides such as sodium hydroxide and potassium hydroxide; and metal carbonates such as potassium carbonate, sodium carbonate, and sodium bicarbonate.

An amount of the base used in the acylation is preferably from 1.0 mol to 50.0 mol, more preferably from 1.0 to 10.0 mol per mol of the 2-isopropenyl-5-methyl-4-hexen-1-ol (5) in view of the economy.

Examples of the catalyst used in the acylation in which the carboxylic anhydride is used as the acylating agent include inorganic acids such as hydrochloric acid, hydrobromic acid, nitric acid, and sulfuric acid; sulfonic acids such as methanesulfonic acid, benzenesulfonic acid, and p-toluenesulfonic acid; Lewis acids such as aluminum trichloride, aluminum isopropoxide, zinc chloride, boron trifluoride, boron trichloride, tin tetrachloride, dibutyltin dichloride, titanium tetrachloride, and titanium(IV) isopropoxide; and metallic acetate salts such as sodium acetate and potassium acetate.

An amount of the catalyst used in the acylation is preferably from 0.001 mol to 1.0 mol, more preferably from 0.005 to 0.2 mol, per mol of 2-isopropenyl-5-methyl-4-hexen-1-ol (5) in view of the economy.

A solvent used in the acylation may be any solvent that does not adversely affect the actions of 2-isopropenyl-5-methyl-4-hexen-1-ol (5), the acylating agent, the base, or the catalyst.

Examples of the solvent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The acylation may be carried out without a solvent, depending on an acylating agent to be used. The solvent may be commercially available one.

An amount of the solvent used in the acylation is preferably from 0.0 g to 2,000.0 g, more preferably from 0.0 g to 500.0 g, per mol of 2-isopropenyl-5-methyl-4-hexen-1-ol (5) in view of the economy.

A reaction temperature in the acylation is preferably from −78° C. to 120° C., more preferably from −30° C. to 80° C., in view of the reactivity and yield.

(B) Dehydration Reaction with a Carboxylic Acid

The dehydration reaction of 2-isopropenyl-5-methyl-4-hexen-1-ol (5) with a carboxylic acid may be carried out typically in the presence of an acid or Lewis acid catalyst.

The carboxylic acid is represented by $R^2$—COOH, wherein $R^2$ is as defined above.

Examples of $R^2$ include linear saturated hydrocarbon groups such as a methyl group, an ethyl group, a 1-propyl group, and a 1-butyl group; branched saturated hydrocarbon groups such as a 2-propyl group, a 2-methylpropyl group, a 2-butyl group, a 2-pentyl group, and a 1,1-dimethylethyl group; linear unsaturated hydrocarbon groups such as a 1-propenyl group, a 1-butenyl group, a 2-butenyl group, a 1-pentenyl group, and a 2-pentenyl group; and branched unsaturated hydrocarbon groups such as a 1-methylpropenyl group, a 2-methylpropenyl group, a 2-methylbutenyl group, and a 2-methyl-2-butenyl group.

Examples of the carboxylic acid used in the dehydration reaction include linear saturated carboxylic acids such as acetic acid and propionic acid; branched saturated carboxylic acids such as 2-methylpropionic acid, 2-methylbutanoic acid, and 3-methylbutanoic acid; linear unsaturated carboxylic acids such as 2-butenoic acid and 2-pentenoic acid; and branched unsaturated carboxylic acids such as 2-methyl-2-butenoic acid and 3-methyl-2-butenoic acid.

Examples of the acid catalyst used in the dehydration reaction include inorganic acids such as hydrochloric acid, hydrobromic acid, nitric acid, and sulfuric acid; and organic acids such as trichloroacetic acid, trifluoroacetic acid, methanesulfonic acid, benzenesulfonic acid, and p-toluenesulfonic acid.

Examples of the Lewis acid catalyst used in the dehydration reaction include aluminum trichloride, dichloroaluminum ethoxide, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide, and titanium (IV) isopropoxide.

The catalyst may be used alone or in combination thereof, if necessary. The catalyst may be commercially available one.

An amount of the catalyst used in the dehydration reaction is preferably from 0.001 to 1.0 mol, more preferably from 0.05 to 0.1 mol, per mol of 2-isopropenyl-5-methyl-4-hexen-1-ol (5) in view of the economy and reactivity.

The dehydration reaction may be carried out while removing water by-produced in the reaction, for example, by azeotropically distilling off the reaction solvent used and water at normal pressure or at a reduced pressure or by adding a dehydrating agent such as anhydrous magnesium sulfate, a molecular sieve, or dicyclohexylcarbodiimide to the reaction mixture.

A solvent used in the dehydration reaction may be any solvent insofar as it does not adversely affect the catalytic activity.

Examples of the solvent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. The solvent may be commercially available one.

An amount of the solvent used in the dehydration reaction is preferably from 0.0 g to 2000.0 g, more preferably from 0.0 g to 500.0 g, per mol of 2-isopropenyl-5-methyl-4-hexen-1-ol (5), in view of the economy.

A reaction temperature in the dehydration may be appropriately set, depending on a catalyst to be used. Typically, the reaction temperature is preferably from −30° C. to 200° C., more preferably from 25 to 100° C. in view of the reactivity and yield. When water by-produced in the reaction is distilled off by azeotropical distillation of the solvent and water, the reaction temperature is preferably the azeotropic point or above of the solvent and water at normal pressure or at a reduced pressure.

(C) Transesterification with a Carboxylate Ester

The transesterification between 2-isopropenyl-5-methyl-4-hexen-1-ol (5) and a carboxylate ester is carried out typically in the presence of a catalyst and can be facilitated by removing an alcohol by-produced from the carboxylate ester, at normal pressure or a reduced pressure.

The carboxylate ester is represented by $R^2COOR^3$, wherein $R^2$ is as defined above, and $R^3$ represents a hydrocarbon group having 1 to 6 carbon atoms.

Examples of $R^2$ in the carboxylate ester used in the transesterification is linear saturated hydrocarbon groups such as a methyl group, an ethyl group, a 1-propyl group, and a 1-butyl group; branched saturated hydrocarbon groups such as a 2-propyl group, a 2-methylpropyl group, a 2-butyl group, a 2-pentyl group, and a 1,1-dimethylethyl group; linear unsaturated hydrocarbon groups such as a 1-propenyl group, a 1-butenyl group, a 2-butenyl group, a 1-pentenyl group, and a 2-pentenyl group; and branched unsaturated hydrocarbon groups such as a 1-methylpropenyl group, a 2-methylpropenyl group, a 2-methylbutenyl group, and a 2-methyl-2-butenyl group.

Examples of $R^3$ in the carboxylate ester include a hydrocarbon group having 1 to 6 carbon atoms, such as a methyl group, an ethyl group, a propyl group, a butyl group, and a phenyl group. Specific examples of the carboxylate ester include methyl carboxylate, ethyl carboxylate, propyl carboxylate, butyl carboxylate, and phenyl carboxylate. The carboxylate ester is preferably methyl carboxylate or ethyl carboxylate in view of the economy, reactivity, and easy removal of an alcohol by-produced from the carboxylate ester.

More specific examples of the carboxylate ester include linear saturated methyl carboxylates such as methyl acetate and methyl propionate; branched saturated methyl carboxylates such as methyl 2-methylpropionate, methyl 2-methylbutanoate, and methyl 3-methylbutanoate; linear unsaturated methyl carboxylates such as methyl 2-butenoate and methyl 2-pentenoate; branched unsaturated methyl carboxylates such as methyl 2-methyl-2-butenoate and methyl 3-methyl-2-butenoate; linear saturated ethyl carboxylates such as ethyl acetate and ethyl propionate; branched saturated ethyl carboxylates such as ethyl 2-methylpropionate, ethyl 2-methylbutanoate, and ethyl 3-methylbutanoate; linear unsaturated ethyl carboxylates such as ethyl 2-butenoate and ethyl 2-pentenoate; and branched unsaturated ethyl carboxylates such as ethyl 2-methyl-2-butenoate and ethyl 3-methyl-2-butenoate.

An amount of the carboxylate ester is preferably from 1.0 to 30.0 mol, more preferably from 1.0 to 5.0 mol, per mol of 2-isopropenyl-5-methyl-4-hexen-1-ol (5).

Examples of the catalyst used in the transesterification include acids such as hydrochloric acid, sulfuric acid, trifluoroacetic acid, methanesulfonic acid, benzenesulfonic acid, p-toluenesulfonic acid, and Amberlyst 15; alkali metal salts of alcohols, such as sodium methoxide, sodium ethoxide, and potassium t-butoxide; metal carboxylates such as sodium acetate, potassium acetate, calcium acetate, tin acetate, zinc acetate, and aluminum acetate; and Lewis acids such as aluminum trichloride, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide, and titanium(IV) isopropoxide.

An amount of the catalyst used in the transesterification is preferably from 0.001 to 1.0 mol, more preferably from 0.005 to 0.1 mol, per mol of 2-isopropenyl-5-methyl-4-hexen-1-ol (5).

A solvent used in the transesterification may be any solvent insofar as it does not adversely affect the action of the catalyst to be used.

Examples of the solvent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. The transesterification may be carried out without a solvent, only with 2-isopropenyl-5-methyl-4-hexen-1-ol (5), a carboxylate ester, and a catalyst. The solvent may be commercially available one.

An amount of the solvent used in the transesterification is preferably from 0.0 g to 2,000.0 g, more preferably from 0.0 g to 500.0 g, per mol of 2-isopropenyl-5-methyl-4-hexen-1-ol (5) in view of the economy.

A reaction temperature in the transesterification may be appropriately selected, depending on the kind of a carboxylate ester and a catalyst to be used. Typically, the reaction temperature is preferably from 0° C. to 200° C., more preferably from 50° C. to 160° C. When the reaction is facilitated by removing an alcohol by-produced from the carboxylate ester, the reaction temperature is preferably a boiling point or above of the alcohol to be removed at normal pressure or a reduced pressure.

(D) Conversion of 2-Isopropenyl-5-Methyl-4-Hexen-1-Ol (5) into an Alkylating Agent, Followed by Acyloxylation with a Carboxylic Acid The conversion of 2-isopropenyl-5-methyl-4-hexen-1-ol (5) into an alkylating agent, followed by acyloxylation with a carboxylic acid is typically carried out by converting the alcohol compound into its corresponding alkylating agent, followed by a reaction with a carboxylic acid in the presence of a base.

Examples of the alkylating agent include halides such as chlorides, bromides, and iodides; and sulfonate esters such as methanesulfonate esters, benzenesulfonate esters, and p-toluenesulfonate esters.

The carboxylic acid is represented by $R^2$—COOH, wherein $R^2$ is as defined above.

Examples of $R^2$ include linear saturated hydrocarbon groups such as a methyl group, an ethyl group, a 1-propyl group, and a 1-butyl group; branched saturated hydrocarbon groups such as a 2-propyl group, a 2-methylpropyl group, a 2-butyl group, a 2-pentyl group, and a 1,1-dimethylethyl group; linear unsaturated hydrocarbon groups such as a 1-propenyl group, a 1-butenyl group, a 2-butenyl group, a 1-pentenyl group, and a 2-pentenyl group; and branched unsaturated hydrocarbon groups such as a 1-methylpropenyl group, a 2-methylpropenyl group, a 2-methylbutenyl group, and a 2-methyl-2-butenyl group.

Examples of the carboxylic acid used in the acyloxylation include linear saturated carboxylic acids such as acetic acid and propionic acid; branched saturated carboxylic acids such as 2-methylpropionic acid, 2-methylbutanoic acid, and 3-methylbutanoic acid; linear unsaturated carboxylic acids such as 2-butenoic acid and 2-pentenoic acid; and branched unsaturated carboxylic acids such as 2-methyl-2-butenoic acid and 3-methyl-2-butenoic acid.

Instead of the carboxylic acid, available metal carboxylate, such as sodium carboxylates and potassium carboxylates, may be used, without using a base.

Examples of the base used in the acyloxylation include amines such as triethylamine, pyridine, N,N-dimethylaminopyridine, and dimethylaniline; organometallic compounds such as n-butyllithium, methyllithium, and phenyllithium; metal hydroxides such as sodium hydroxide and potassium hydroxide; metal carbonates such as potassium carbonate, sodium carbonate, and sodium bicarbonate; and metal hydrides such as sodium hydride and potassium hydride.

An amount of the base used in the acyloxylation is preferably from 1.0 mol to 50.0 mol, more preferably from 1.0 to 10.0 mol, per mol of 2-isopropenyl-5-methyl-4-hexen-1-ol (5) in view of the economy.

Any solvent may be used in the acyloxylation insofar as it does not give adverse effect to the reactive species.

Examples of the solvent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The acyloxylation may be carried out without a solvent, depending on the kind of an alkylating agent and/or base to be used. The solvent may be commercially available one.

An amount of the solvent used in the acyloxylation is preferably from 0.0 g to 2,000.0 g, more preferably from 0.0 g to 500.0 g, per mol of 2-isopropenyl-5-methyl-4-hexen-1-ol in view of the economy.

A reaction temperature in the acyloxylation is preferably from −30° C. to 250° C., more preferably from 25° C. to 180° C., in view of the reactivity and yield.

$R^2$ in the general formula (6) represents a linear or branched monovalent hydrocarbon group having 1 to 6, preferably 1 to 4 carbon atoms. $R^2$ is derived from the acylating agent used in the aforesaid (A), the carboxylic acid used in (B) or (D), and the carboxylate ester used in (C).

Examples of the hydrocarbon group, $R^2$, include linear saturated hydrocarbon groups such as a methyl group, an ethyl group, a 1-propyl group, and a 1-butyl group; branched saturated hydrocarbon groups such as a 2-propyl group, a 2-methylpropyl group, a 2-butyl group, a 2-pentyl group, and a 1,1-dimethylethyl group; linear unsaturated hydrocarbon groups such as a 1-propenyl group, a 1-butenyl group, a 2-butenyl group, a 1-pentenyl group, and a 2-pentenyl group; and branched unsaturated hydrocarbon groups such as a 1-methylpropenyl group, a 2-methylpropenyl group, a 2-methylbutenyl group, and a 2-methyl-2-butenyl group.

Examples of the 2-isopropenyl-5-methyl-4-hexen-1-yl carboxylate (6) include linear saturated carboxylate esters such as 2-isopropenyl-5-methyl-4-hexen-1-yl acetate, 2-isopropenyl-5-methyl-4-hexen-1-yl propionate, and 2-isopropenyl-5-methyl-4-hexen-1-yl butanoate; branched saturated carboxylate esters such as 2-isopropenyl-5-methyl-4-hexen-1-yl 2-methylpropionate, 2-isopropenyl-5-methyl-4-hexen-1-yl 2-methylbutanoate, 2-isopropenyl-5-methyl-4-hexen-1-yl 3-methylbutanoate, and 2-isopropenyl-5-methyl-4-hexen-1-yl 2,2-dimethylpropionate; linear unsaturated carboxylate esters such as 2-isopropenyl-5-methyl-4-hexen-1-yl 2-butenoate, 2-isopropenyl-5-methyl-4-hexen-1-yl 2-pentenoate, and 2-isopropenyl-5-methyl-4-hexen-1-yl 3-pentenoate; and branched unsaturated carboxylate esters such as 2-isopropenyl-5-methyl-4-hexen-1-yl 2-methyl-2-butenoate and 2-isopropenyl-5-methyl-4-hexen-1-yl 3-methyl-2-butenoate.

Among the 2-isopropenyl-5-methyl-4-hexen-1-yl carboxylate (6), the following was identified as a sex pheromone component of mealybugs: 2-isopropenyl-5-methyl-4-hexen-1-yl 3-methyl-2-butenoate identified for vine mealybug (scientific name: *Planococcus ficus*); 2-isopropenyl-5-methyl-4-hexen-1-yl acetate and 2-isopropenyl-5-methyl-4-hexen-1-yl propionate identified for banana mealybug (scientific name: *Dysmicoccu grassii*); and 2-isopropenyl-5-methyl-4-hexen-1-yl 2-methylbutanoate identified for pink hibiscus mealybug (scientific name: *Maconelhcoccus hirsutus*) and madeira mealybug (scientific name: *Phenacoccus madeirensis*).

The 2-isopropenyl-5-methyl-4-hexen-1-yl carboxylate (6) includes an enantiomer and a diastereomer thereof, and equimolar or non-equimolar mixtures thereof.

Thus, 2-isopropenyl-5-methyl-4-hexenoic acid, 2-isopropenyl-5-methyl-4-hexen-1-ol known as a perfume, and 2-isopropenyl-5-methyl-4-hexenyl carboxylates which are sex pheromone substances of mealybugs, are prepared industrially, conveniently, and economically.

EXAMPLES

The present invention will be further described with reference to the following Synthetic Examples, Examples, and Comparative Examples. It should be understood that the present invention is not limited to or by the Examples.

The term "purity" as used herein means an area percentage in gas chromatography (hereinafter referred to also as "GC"), unless otherwise specified. The term "production ratio" means a ratio of area percentages in GC.

The term "yield" is calculated from the area percentages determined by GC.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

The term "conversion" is calculated from a sum of area percentages of raw materials and a target compound and an area percentage of the target compound, determined by GC.

GC conditions were as follows:

GC Conditions for Monitoring Reactions (Examples 1 to 5 and Comparative Examples 1 to 3)

GC: Capillary gas chromatograph GC-2010 (Shimadzu Corporation); column: DB-5, 0.25 mm×0.25 mmϕ×30 m; carrier gas: He (1.55 mL/min), detector: FID; column temperature: held at 70° C. for 3 minutes, elevated in a rate of 10° C./min, and up to 250° C.

GC Conditions for Determining a Production Ratio of 2-isopropylidene-5-methyl-4-hexenoic acid (4) (Examples 1 to 5 and Comparative Examples 1 to 3)

GC: Capillary gas chromatograph GC-2010 (Shimadzu Corporation); column: DB-WAX, 0.25 mm×0.25 mmϕ×30 m; carrier gas: He (1.55 mL/min), detector: FID; column temperature: held at 120° C. for 12 minutes, elevated in a rate of 20° C./min, and up to 230° C.

GC Conditions for Monitoring the Formation of 2-isopropenyl-5-methyl-4-hexen-1-ol (5) (Examples 6 to 10)

GC: Capillary gas chromatograph GC-2010 (Shimadzu Corporation); column: DB-5, 0.25 mm×0.25 mmϕ×30 m; carrier gas: He (1.55 mL/min), detector: FID; column temperature: held at 100° C. for 3 minutes, elevated in a rate of 10° C./min, and up to 250° C.

Synthetic Example 1: Preparation of 2-methyl-3-buten-2-yl 3-methyl-2-butenoate (3)

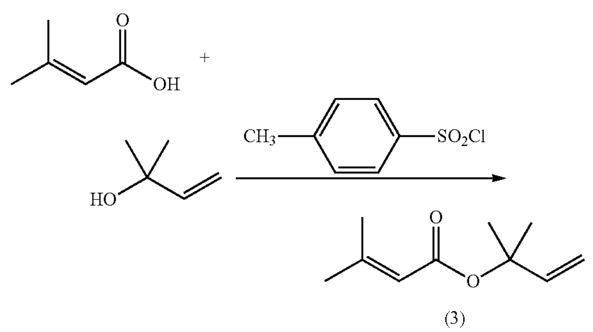

Air in a reactor equipped with a stirrer, a condenser and a thermometer was purged with a nitrogen gas. Then, to the reactor were placed 3-methyl-2-butenoic acid (100.1 g: 1.00 mol), p-toluenesulfonyl chloride (247.9 g: 1.30 mol), and toluene (300.0 g), and heated to 50° C. To the reaction mixture, pyridine (300.6 g: 3.8 mol) was added dropwise at a reaction mixture temperature of 50° C. to 60° C. over 2 hours. After the completion of the dropwise addition, the reaction mixture was stirred at a reaction mixture temperature of 60° C. for 1 hour. Then, 2-methyl-3-buten-2-ol (103.4 g: 1.2 mol) was added dropwise to the reaction mixture at a reaction mixture temperature of 65° C. to 70° C. over 1 hour. Then, the reaction mixture was stirred at a reaction mixture temperature of 68 to 70° C. for 8 hours. Then, the reaction mixture temperature was lowered to 55 to 60° C. Water (185.0 g) was then added to quench the reaction. Then, an aqueous phase was separated, and an organic phase was washed with an aqueous 5.0 wt % sodium hydroxide solution (250.0 g), and then with an aqueous 5.0 wt % sodium chloride solution (250.0 g). The solvent was removed from the organic phase at a reduced pressure and then the residue was purified by distillation to obtain 2-methyl-3-buten-2-yl 3-methyl-2-butenoate (3) (143.0 g: 0.85 mol, yield 84.9%, purity 97.9%).

The following are spectrum data of the 2-methyl-3-buten-2-yl 3-methyl-2-butenoate (3) thus prepared.

Nuclear magnetic resonance spectrum: $^1$H-NMR (500 MHz, $CDCl_3$): δ 1.52 (6H, s), 1.85 (3H, d, J=1.6 Hz), 2.12 (d, J=1.5 Hz), 5.05 (1H, dd, J=10.9, 0.9 Hz), 5.07 (1H, dd, J=10.9, 0.8 Hz), 5.15 (1H, dd, J=17.5, 0.8 Hz), 5.61-5.63 (1H, m), 6.09 (1H, dd, J=17.5, 10.7 Hz) ppm.

$^{13}$C-NMR (126 MHz, $CDCl_3$): δ 19.93, 26.65, 27.30, 79.76, 112.65, 117.17, 143.07, 155.61, 165.74 ppm.

Mass spectrum: EI (70 eV): m/z 168 ($M^+$), 153, 123, 101, 83, 88, 55, 41, 27.

Infrared absorption spectrum (ATR method): ν ($cm^{-1}$) 680, 776, 852, 921, 976, 1075, 1123, 1232, 1285, 1351, 1363, 1379, 1414, 1446, 1653, 1719, 2938, 1979, 3089.

Synthetic Example 2: Preparation of 2-methyl-3-buten-2-yl 3-methyl-2-butenoate (3)

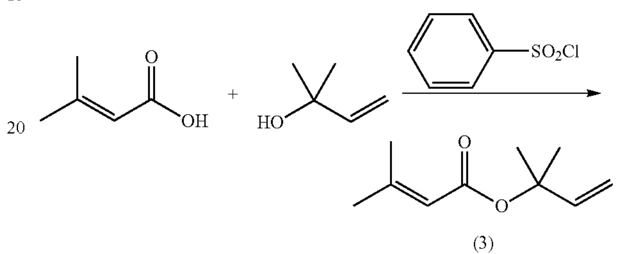

The procedures of Synthetic Example 1 were repeated with the exception that benzenesulfonyl chloride (229.6 g: 1.30 mol) was used instead of p-toluenesulfonyl chloride, to obtain 2-methyl-3-buten-2-yl 3-methyl-2-butenoate (3) (149.7 g: 0.89 mol, yield 89.1%, purity 95.5%).

The various spectrum data of 2-methyl-3-buten-2-yl 3-methyl-2-butenoate (3) thus prepared were the same as those obtained in Synthetic Example 1.

Synthetic Example 3: Preparation of 2-isopropylidene-5-methyl-4-hexenoic acid

2-Isopropylidene-5-methyl-4-hexenoic acid, which is a regioisomer of 2-isopropenyl-5-methyl-4-hexenoic acid (4), was synthesized in the following known methods, Synthetic Examples 3-1 and 3-2 below, and used as a reference material.

Synthetic Example 3-1: Synthesis of t-butyl 2-isopropylidene-5-methyl-4-hexenoate

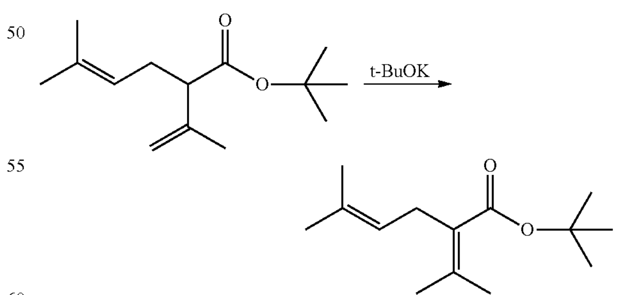

To a mixture of t-butyl 2-isopropenyl-5-methyl-4-hexenoate (256.8 g, purity 81.9%) and t-butyl alcohol (1000 ml) was added potassium t-butoxide (25.0 g) at room temperature in a nitrogen atmosphere and stirred at room temperature overnight. The mixture was poured into ice water and subjected to extraction with n-hexane. The extract was subjected to post-treatments, i.e., washing, drying, and concentration, to obtain a crude product (228.65 g, 81.5% purity, t-butyl 2-isopropenyl-5-methyl-4-hexenoate: t-butyl 2-isopropylidene-5-methyl-4-hexenoate=10.2:89.8). This crude product was purified by distillation at a reduced pressure to obtain t-butyl 2-isopropylidene-5-methyl-4-hexenoate (34.34 g, purity 94.2%).

The following are spectrum data of the t-butyl 2-isopropylidene-5-methyl-4-hexenoate thus prepared.

Nuclear magnetic resonance spectrum: $^{1}$H-NMR (500 MHz, $CDCl_3$): δ=1.47 (9H, s), 1.65-1.67 (6H, m), 1.76 (3H, s), 1.90 (3H, s), 2.94 (2H, d, J=6.8 Hz), 5.04-5.07 (1H, m) ppm.

Infrared absorption spectrum (D-ATR): ν=2977, 2928, 2859, 1711, 1367, 1158, 1073 $cm^{-1}$.

Synthetic Example 3-2: Synthesis of 2-isopropylidene-5-methyl-4-hexenoic acid

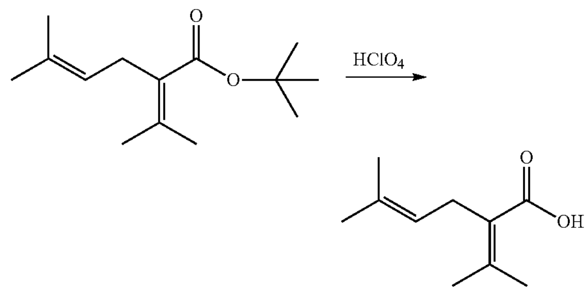

To a mixture of t-butyl 2-isopropylidene-5-methyl-4-hexenoate obtained in Synthetic Example 3-1 (97.0 g, 87.9% purity) and tetrahydrofuran (2000 ml) was added 22.5% perchloric acid (160 ml) in a nitrogen atmosphere, and stirred at a reaction mixture temperature of 60° C. to 80° C. for 25 hours. The mixture was poured into ice water and subjected to extraction with n-hexane. The extract was subjected to extraction twice with an aqueous 10% sodium hydroxide solution (100 ml). To the aqueous phase separated was added 20% hydrochloric acid (100 ml) and subjected to extraction with a mixture of tetrahydrofuran and toluene of a volume ratio of 1:1. Then, the resulting organic phase was subjected to post-treatments, i.e., washing, drying, and concentration, to obtain a crude product of the target compound (29.57 g, purity 94.6%, yield 44%).

This crude product was recrystallized from n-hexane to obtain 2-isopropylidene-5-methyl-4-hexenoic acid (15.69 g, purity 98.0%).

The following are spectrum data of the 2-isopropylidene-5-methyl-4-hexenoic acid thus prepared.

Nuclear magnetic resonance spectrum: $^{1}$H-NMR (500 MHz, $CDCl_3$): δ=1.67-1.69 (6H, m), 1.87 (3H, s), 2.10 (3H, s), 3.03 (2H, d, J=6.9 Hz), 5.03-5.07 (1H, m), 11.90-12.70 (1H, br. s) ppm.

$^{13}$C-NMR (125 MHz, $CDCl_3$): δ=17.79, 23.00, 23.49, 25.68, 28.75, 121.80, 126.02, 132.07, 147.80, 175.03 ppm.

Mass spectrum: EI (70 eV): m/z 168 ($M^+$), 153, 135, 125, 123, 107, 95, 81, 67, 55, 41, 27.

Infrared absorption spectrum (D-ATR): ν=2996, 2966, 2923, 1683, 1611, 1292, 1236, 932 $cm^{-1}$.

Example 1: Preparation of 2-isopropenyl-5-methyl-4-hexenoic acid (4)

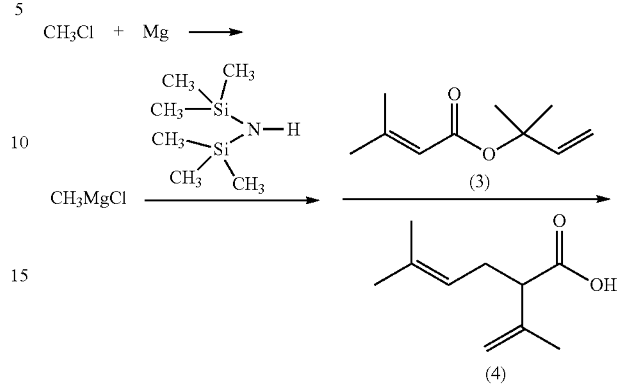

Air in a reactor equipped with a stirrer, a condenser and a thermometer was purged with a nitrogen gas. Then, to the reactor were placed metal magnesium (29.2 g: 1.20 mol) and tetrahydrofuran (455.0 g), and heated to 45° C. Gaseous methyl chloride (63.6 g: 1.26 mol) was fed to the reaction mixture at a reaction mixture temperature of 58° C. to 60° C. over 5 hours. After the completion of the feeding, the reaction mixture was stirred at a reaction mixture temperature of 60° C. for 1 hour to prepare Grignard reagent (1).

The temperature of the prepared Grignard reagent (1) was adjusted to 25° C., to which 1,1,1,3,3,3-hexamethyldisilazane (209.8 g: 1.30 mol) was added dropwise at a reaction mixture temperature of 25° C. to 30° C. over 2 hours. After the completion of the dropwise addition, the reaction mixture was stirred at a reaction mixture temperature of 30° C. for 2 hours.

The reaction mixture was heated to 40° C., and 2-methyl-3-buten-2-yl 3-methyl-2-butenoate (3) (168.2 g: 1.00 mol) was added dropwise at a reaction mixture temperature of 40° C. to 45° C. over 2 hours. After the completion of the dropwise addition, the reaction mixture was stirred at a reaction mixture temperature of 45° C. to 50° C. for 10 hours. The reaction mixture was cooled to 20° C., and then 13.0 wt % hydrochloric acid (720.0 g) was added to quench the reaction. The aqueous phase was separated, and an aqueous 12.0 wt % sodium hydroxide solution (382.0 g) and toluene (93.0 g) were placed to the organic phase, followed by phase separation to obtain the organic phase and the aqueous phase. The resulting aqueous phase was made acid by dropwise addition of 20.0 wt % hydrochloric acid (250.0 g). Then, toluene (220.0 g) was added and subjected to extraction, and the aqueous phase was removed. The resulting organic phase was washed with an aqueous 6.5 wt % sodium chloride solution (268.0 g) twice. The solvent was removed from the washed organic phase at a reduced pressure to obtain 2-isopropenyl-5-methyl-4-hexenoic acid (4) (163.2 g: 0.97 mol, yield 96.5%, purity 95.9%, conversion 99.9%).

The following are spectrum data of the 2-isopropenyl-5-methyl-4-hexenoic acid (4) thus prepared.

Nuclear magnetic resonance spectrum: $^{1}$H-NMR (500 MHz, $CDCl_3$): δ 1.63 (3H, s), 1.69 (3H, d, J=1.1 Hz), 1.79 (3H, s), 2.28 (1H, quint, J=7.3 Hz), 2.52 (1H, quint, J=7.5 Hz), 3.05 (1H, t, J=7.7 Hz), 4.93-4.95 (2H, m), 5.05 (1H, tt, J=6.5, 1.3 Hz), 11.7 (1H, brs) ppm.

$^{13}$C-NMR (126 MHz, $CDCl_3$): δ 17.80, 20.38, 25.73, 28.70, 53.10, 114.29, 120.77, 133.81, 141.84, 180.06 ppm.

Mass spectrum: EI (70 eV): m/z 168 ($M^+$), 100, 81, 69, 53, 41, 27.

Infrared absorption spectrum (ATR method): ν ($cm^{-1}$) 578, 744, 774, 899, 1110, 1207, 1251, 1288, 1378, 1413, 1440, 1647, 1707, 2917, 2973, 3081.

The GC results of the obtained product showed that 2-isopropylidene-5-methyl-4-hexenoic acid, which is a regioisomer of 2-isopropenyl-5-methyl-4-hexenoic acid (4), was not formed.

The obtained 2-isopropenyl-5-methyl-4-hexenoic acid (4) was used as such, without being purified, in a subsequent step.

Example 2: Preparation of 2-isopropenyl-5-methyl-4-hexenoic acid (4)

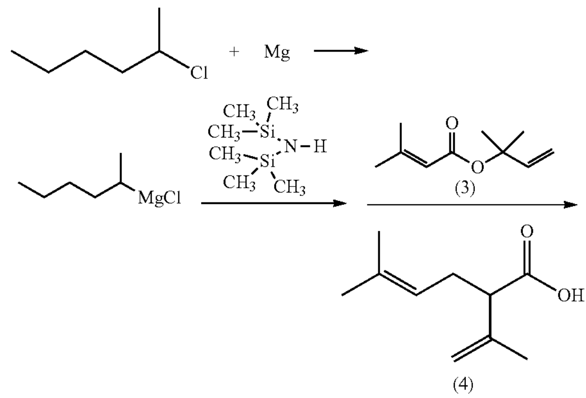

Air in a reactor equipped with a stirrer, a condenser and a thermometer was purged with a nitrogen gas. Then, to the reactor were placed metal magnesium (30.4 g: 1.25 mol) and tetrahydrofuran (450.0 g), and heated to 65° C. To the reaction mixture, dibromoethane (1.9 g: 0.01 mol) was added, and then 2-hexyl chloride (144.7 g: 1.20 mol) was added dropwise at a reaction mixture temperature of 60° C. to 70° C. over 5 hours. After the completion of the dropwise addition, the reaction mixture was stirred at a reaction mixture temperature of 75 to 80° C. for 3 hours to prepare Grignard reagent (1).

The procedures of Example 1 after the preparation of the Grignard reagent were repeated to obtain 2-isopropenyl-5-methyl-4-hexenoic acid (4) (158.0 g: 0.94 mol, yield 93.9%, purity 95.3%, conversion 98.2%).

The various spectrum data of 2-isopropenyl-5-methyl-4-hexenoic acid (4) thus prepared were the same as those obtained in Example 1.

The GC results of the obtained product showed that 2-isopropylidene-5-methyl-4-hexenoic acid, which is a regioisomer of 2-isopropenyl-5-methyl-4-hexenoic acid (4), was not formed.

The obtained 2-isopropenyl-5-methyl-4-hexenoic acid (4) was used as such, without being purified, in a subsequent step.

Example 3: Preparation of 2-isopropenyl-5-methyl-4-hexenoic acid (4)

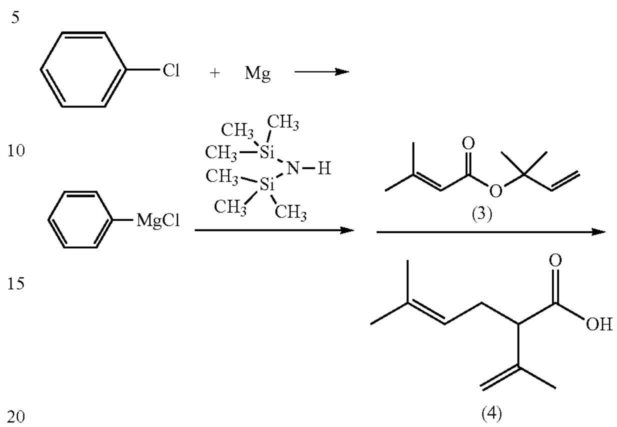

The procedures of Example 2 were repeated with the exception that phenyl chloride (135.1 g: 1.20 mol) was used instead of 2-hexyl chloride as an organohalide to obtain 2-isopropenyl-5-methyl-4-hexenoic acid (4) (154.7 g: 0.92 mol, yield 91.9%, purity 95.2%, conversion 95.1%).

The various spectrum data of 2-isopropenyl-5-methyl-4-hexenoic acid (4) thus prepared were the same as those obtained in Example 1.

The GC results of the obtained product showed that 2-isopropylidene-5-methyl-4-hexenoic acid, which is a regioisomer of 2-isopropenyl-5-methyl-4-hexenoic acid (4), was not formed.

The obtained 2-isopropenyl-5-methyl-4-hexenoic acid (4) was used as such, without being purified, in a subsequent step.

Example 4: Preparation of 2-isopropenyl-5-methyl-4-hexenoic acid (4)

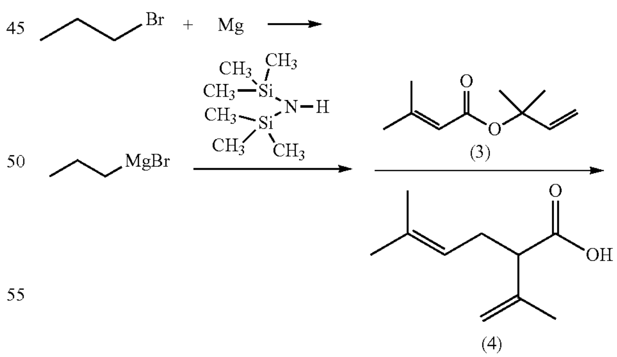

The procedures of Example 2 were repeated with the exception that 1-propyl bromide (147.6 g: 1.20 mol) was used instead of 2-hexyl chloride as an organohalide to obtain 2-isopropenyl-5-methyl-4-hexenoic acid (4) (134.6 g: 0.80 mol, yield 80.0%, purity 89.8%, conversion 99.6%).

The various spectrum data of 2-isopropenyl-5-methyl-4-hexenoic acid (4) thus prepared were the same as those obtained in Example 1.

The GC results of the obtained product showed that 2-isopropylidene-5-methyl-4-hexenoic acid, which is a regioisomer of 2-isopropenyl-5-methyl-4-hexenoic acid (4), was not formed.

The obtained 2-isopropenyl-5-methyl-4-hexenoic acid (4) was used as such, without being purified, in a subsequent step.

Example 5: Preparation of 2-isopropenyl-5-methyl-4-hexenoic acid (4)

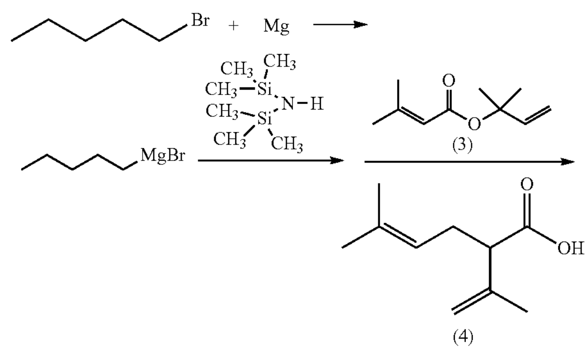

The procedures of Example 2 were repeated with the exception that 1-pentyl bromide (181.3 g: 1.20 mol) was used instead of 2-hexyl chloride as an organohalide to obtain 2-isopropenyl-5-methyl-4-hexenoic acid (4) (144.7 g: 0.86 mol, yield 86.0%, purity 91.2%, conversion 99.0%).

The various spectrum data of 2-isopropenyl-5-methyl-4-hexenoic acid (4) thus prepared were the same as those obtained in Example 1.

The GC results of the obtained product showed that a regioisomer, 2-isopropylidene-5-methyl-4-hexenoic acid, was not formed. The obtained 2-isopropenyl-5-methyl-4-hexenoic acid (4) was used as such, without being purified, in a subsequent step.

Example 6: Preparation of 2-isopropenyl-5-methyl-4-hexen-1-ol (5) from 2-isopropenyl-5-methyl-4-hexenoic acid (4)

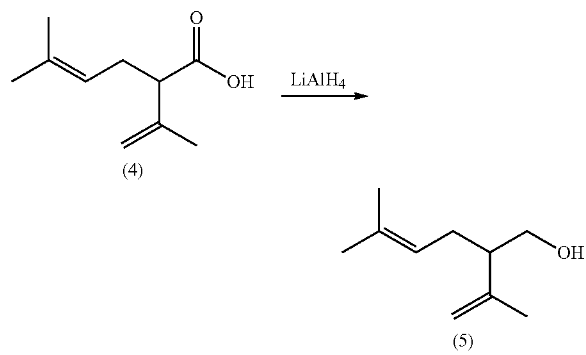

Air in a reactor equipped with a stirrer, a condenser and a thermometer was purged with a nitrogen gas. Then, to the reactor were placed lithium aluminum hydride (47.4 g: 1.25 mol) and tetrahydrofuran (1,089.0 g), and the mixture was stirred at a reaction mixture temperature of 20 to 25° C. for 2 hours to disperse the lithium aluminum hydride. The dispersion temperature was lowered to 0° C. to 5° C., and a solution of 2-isopropenyl-5-methyl-4-hexenoic acid (4) obtained according to Example 1 (168.2 g: 1.00 mol) in tetrahydrofuran (290.0 g) was added dropwise at a reaction mixture temperature of 10° C. to 15° C. over 1.5 hours. After the completion of the dropwise addition, the reaction mixture was stirred at a reaction mixture temperature of 10° C. to 15° C. for 1 hour and then at a reaction mixture temperature of 25° C. to 30° C. for 2 hours. The reaction mixture was cooled to 5° C. or below, and then water (47.5 g), an aqueous 10 wt % sodium hydroxide solution (190.0 g), and tetrahydrofuran (150.0 g) were successively added dropwise at a reaction mixture temperature of 0° C. to 15° C. After the completion of the dropwise addition, the reaction mixture was stirred at a reaction mixture temperature of 25° C. to 35° C. for 1 hour. After the stirring, the reaction mixture was filtered, and the solvent was removed from the filtrate at a reduced pressure to obtain 2-isopropenyl-5-methyl-4-hexen-1-ol (5) (148.1 g: 0.96 mol, yield 96.0%, purity 93.6%).

The following are spectrum data of the 2-isopropenyl-5-methyl-4-hexen-1-ol (5) thus prepared.

Nuclear magnetic resonance spectrum: $^{1}H$-NMR (500 MHz, $CDCl_3$): δ 1.53 (1H, s), 1.60 (3H, s), 1.68 (6H, s), 1.99-2.13 (2H, m), 2.24-2.29 (1H, m), 3.48 (1H, dd, J=10.7, 8.0 Hz), 3.55 (1H, dd, J=10.7, 5.0 Hz), 4.80 (1H, s), 4.91 (1H, s), 5.07 (1H, t, J=7.1 Hz) ppm.

$^{13}C$-NMR (126 MHz, $CDCl_3$): δ 17.79, 19.44, 25.70, 28.32, 49.91, 63.57, 113.10, 121.98, 132.72, 145.36 ppm.

Mass spectrum: EI (70 eV): m/z 154 ($M^+$), 136, 123, 121, 111, 93, 83, 81, 69, 53, 41, 29.

Infrared absorption spectrum (ATR method): ν ($cm^{-1}$) 594, 720, 778, 838, 889, 1039, 1111, 1199, 1280, 1337, 1376, 1415, 1441, 1645, 1673, 1730, 2728, 2616, 1667, 3073, 3362.

The obtained 2-isopropenyl-5-methyl-4-hexen-1-ol (5) was used as such, without being purified, in a subsequent step.

Example 7: Preparation of 2-isopropenyl-5-methyl-4-hexen-1-yl 3-methyl-2-butenoate (6: $R^2$=2-Methylpropenyl Group) from 2-isopropenyl-5-methyl-4-hexen-1-ol (5) (this Preparation Embodiment Corresponds to the Aforesaid (D): Conversion of 2-isopropenyl-5-methyl-4-hexen-1-ol (5) into an Alkylating Agent, Followed by Acyloxylation with a Carboxylic Acid)

Example 7-1: A Process for Preparing 2-isopropenyl-5-methyl-4-hexen-1-yl methanesulfonate

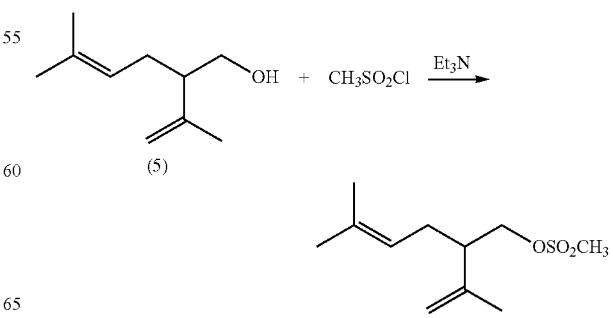

Air in a reactor equipped with a stirrer, a condenser and a thermometer was purged with a nitrogen gas. Then, to the reactor were placed 2-isopropenyl-5-methyl-4-hexen-1-ol (5) obtained in Example 6 (154.3 g: 1.00 mol), triethylamine (109.3 g: 1.08 mol), and methylene chloride (500.0 g), and the reaction mixture temperature was lowered to 0° C. to 5° C. To the reaction mixture, methanesulfonyl chloride (121.4 g: 1.06 mol) was added dropwise at a reaction mixture temperature of 10° C. to 20° C. over 2 hours. After the completion of the dropwise addition, the reaction mixture was stirred at a reaction mixture temperature of 20° C. to 25° C. for 2 hours. Then, water (200.0 g) was added to quench the reaction. The mixture was subjected to extraction with n-hexane (280.0 g), and the aqueous phase was separated. The organic phase was washed with an aqueous 1.3 wt % sodium bicarbonate solution (170.0 g), and then with an aqueous 5.0 wt % sodium chloride solution (175.0 g). The solvent was then removed at a reduced pressure to obtain 2-isopropenyl-5-methyl-4-hexen-1-yl methanesulfonate (228.9 g: 0.99 mol, yield 99.4%, purity 94.7%).

The obtained 2-isopropenyl-5-methyl-4-hexen-1-yl methanesulfonate was used as such, without being purified, in a subsequent step.

Example 7-2: A Process for Preparing 2-isopropenyl-5-methyl-4-hexen-1-yl 3-methyl-2-butenoate (6: $R^2$=2-Methylpropenyl Group) from 2-isopropenyl-5-methyl-4-hexen-1-yl methanesulfonate

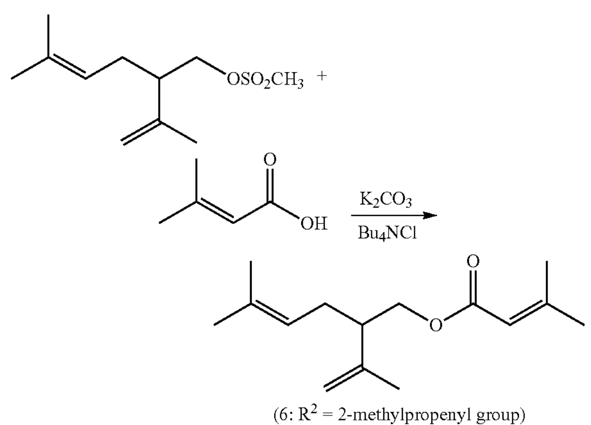

(6: $R^2$ = 2-methylpropenyl group)

Air in a reactor equipped with a stirrer, a condenser and a thermometer was purged with a nitrogen gas. Then, to the reactor were placed 3-methyl-2-butenoic acid (120.1 g: 1.20 mol), potassium carbonate (105.0 g: 0.76 mol), tetrabutylammonium chloride (11.1 g: 0.04 mol), toluene (730.0 g), and water (8.4 g), and heated to a reaction mixture temperature of 95° C. to 100° C. and stirred for 1 hour. To the reaction mixture, a solution of 2-isopropenyl-5-methyl-4-hexen-1-yl methanesulfonate obtained according to Example 7-1 (230.3 g: 1.00 mol) in toluene (138.0 g) was added dropwise at a reaction mixture temperature of 95° C. to 100° C. over 3 hours. After the completion of the dropwise addition, the reaction mixture was stirred at a reaction mixture temperature of 95° C. to 100° C. for 5 hours. The reaction mixture temperature was lowered to 25 to 30° C., and water (450.0 g) was then added to quench the reaction. Then, the aqueous phase was separated, and the organic phase was washed with water (280.0 g), and then with an aqueous 5.0 wt % sodium chloride solution (280.0 g). The solvent was removed from the organic phase at a reduced pressure and the residue was purified by distillation to obtain 2-isopropenyl-5-methyl-4-hexen-1-yl 3-methyl-2-butenoate (6: $R^2$=2-methylpropenyl group) (214.2 g: 0.91 mol, yield 90.6%, purity 94.7%).

The following are spectrum data of the 2-isopropenyl-5-methyl-4-hexen-1-yl 3-methyl-2-butenoate (6: $R^2$=2-methylpropenyl group) thus prepared.

Nuclear magnetic resonance spectrum: $^1$H-NMR (500 MHz, $CDCl_3$): δ 1.59 (3H, s), 1.67 (3H, s), 1.70 (3H, s), 1.88 (3H, d, J=1.5 Hz), 2.06 (1H, quint, J=7.2 Hz), 2.12-2.20 (4H, m), 2.41 (1H, quint, J=7.1 Hz), 4.02-4.09 (2H, m), 4.74 (1H, s), 4.82 (1H, s), 5.06 (1H, t, J=7.6 Hz), 5.65 (1H, s) ppm.

$^{13}$C-NMR (126 MHz, $CDCl_3$): δ 17.79, 19.94, 20.17, 25.72, 27.34, 28.67, 46.14, 65.09, 112.23, 116.09, 121.73, 132.79, 145.08, 156.37, 166.70 ppm.

Mass spectrum: EI (70 eV): m/z 236 ($M^+$), 136 ($M^+$-C4H7CO2H), 121, 107, 95, 83, 69, 55, 41, 29.

Infrared absorption spectrum (ATR method): ν ($cm^{-1}$) 850, 891, 1006, 1077, 1145, 1226, 1269, 1347, 1377, 1447, 1650, 1719, 2915, 2970.

Example 8: A Process for Preparing 2-isopropenyl-5-methyl-4-hexen-1-yl acetate (6: $R^2$=Methyl Group) from 2-isopropenyl-5-methyl-4-hexen-1-ol (5) (this Process Corresponds to the Aforesaid (A): Acylation with an Acylating Agent)

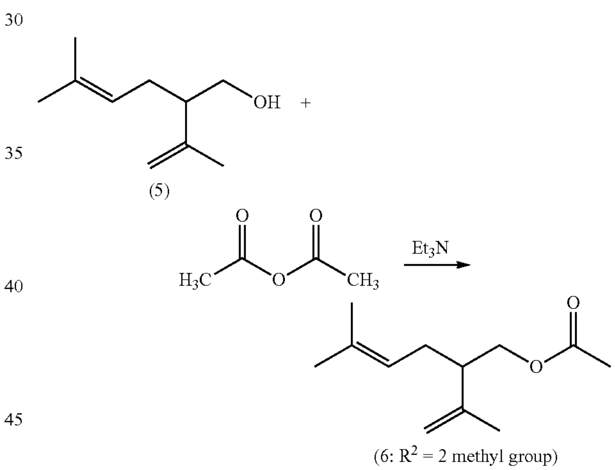

(6: $R^2$ = 2 methyl group)

Air in a reactor equipped with a stirrer, a condenser and a thermometer was purged with a nitrogen gas. Then, to the reactor were placed 2-isopropenyl-5-methyl-4-hexen-1-ol (5) obtained according to Example 6 (154.3 g: 1.00 mol), triethylamine (202.4 g: 2.00 mol), and methylene chloride (850.0 g). After the completion of the addition, the reaction mixture temperature was lowered to 0° C. to 5° C. To the reaction mixture, acetic anhydride (153.14 g: 1.50 mol) was added dropwise at a reaction mixture temperature of 5° C. to 10° C. over 1 hour. After the completion of the dropwise addition, the reaction mixture was stirred at a reaction mixture temperature of 10° C. to 25° C. for 3 hours. The reaction mixture temperature was lowered to 0° C. to 5° C., and water (650.0 g) was then added to quench the reaction. Then, the aqueous phase was separated, and the organic phase was successively washed with 5.0 wt % hydrochloric acid (800.0 g), water (1000.0 g), and an aqueous 5.0 wt % sodium bicarbonate solution (1,000.0 g). The solvent was removed from the organic phase at a reduced pressure and the residue was purified by distillation to obtain 2-isopropenyl-5-methyl-4-hexen-1-yl acetate (6: $R^2$=methyl group) (154.2 g: 0.79 mol, yield 78.6%, purity 98.8%).

The following are spectrum data of the 2-isopropenyl-5-methyl-4-hexen-1-yl acetate (6: $R^2$=methyl group) thus prepared.

Nuclear magnetic resonance spectrum: $^1$H-NMR (500 MHz, $CDCl_3$): δ 1.59 (3H, s), 1.67 (3H, s), 1.68 (3H, s), 2.01-2.06 (4H, m), 2.14 (1H, quint, J=7.0 Hz), 2.38 (1H, quint, J=7.0 Hz), 4.03 (2H, d, J=6.9 Hz), 4.73 (1H, s), 4.82 (1H, quint, J=1.5 Hz) 5.06 (1H, tt, J=7.3, 1.3 Hz) ppm.

$^{13}$C-NMR (126 MHz, $CDCl_3$): δ 17.76, 19.88, 20.91, 25.70, 28.54, 46.02, 65.80, 112.33, 121.55, 132.89, 144.83, 171.04 ppm.

Mass spectrum: EI (70 eV): m/z 196 ($M^+$), 136, 121, 107, 93, 80, 69, 53, 43, 41, 27.

Infrared absorption spectrum (ATR method): ν ($cm^{-1}$) 606, 639, 893, 974, 1039, 1240, 1364, 1377, 1449, 1647, 1743, 2917, 2970, 3075.

Example 9: A Process for Preparing 2-isopropenyl-5-methyl-4-hexen-1-yl propionate (6: $R^2$=Ethyl Group) from 2-isopropenyl-5-methyl-4-hexen-1-ol (5) (this Process Corresponds to the Aforesaid (A): Acylation with an Acylating Agent)

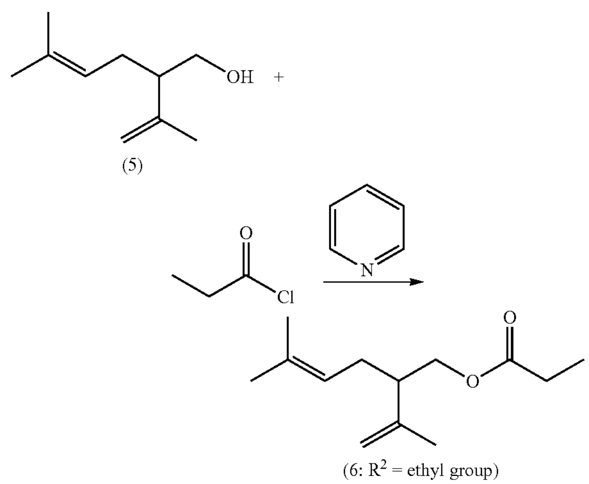

Air in a reactor equipped with a stirrer, a condenser and a thermometer was purged with a nitrogen gas. Then, to the reactor were placed 2-isopropenyl-5-methyl-4-hexen-1-ol (5) obtained according to Example 6 (154.3 g: 1.00 mol), pyridine (118.7 g: 1.50 mol), and toluene (530.0 g). After the completion of the addition, the reaction mixture temperature was lowered to 0° C. to 5° C. To the reaction mixture, propionyl chloride (111.0 g: 1.20 mol) was added dropwise at a reaction mixture temperature of 5° C. to 10° C. over 3 hours. After the completion of the dropwise addition, the reaction mixture was stirred at a reaction mixture temperature of 5° C. to 10° C. for 3 hours. The reaction mixture temperature was lowered to 0° C. to 5° C., and water (340.0 g) was then added to quench the reaction. Then, the aqueous phase was separated, and the organic phase was successively washed with 5.0 wt % hydrochloric acid (500.0 g), an aqueous 5.0 wt % sodium chloride solution (350.0 g), and an aqueous 5.0 wt % sodium bicarbonate solution (350.0 g). The solvent was removed from the organic phase at a reduced pressure and the residue was purified by distillation to obtain 2-isopropenyl-5-methyl-4-hexen-1-yl propionate (6: $R^2$=ethyl group) (165.73 g: 0.79 mol, yield 78.8%, purity 98.8%).

The following are spectrum data of the 2-isopropenyl-5-methyl-4-hexen-1-yl propionate (6: $R^2$=ethyl group) thus prepared.

Nuclear magnetic resonance spectrum: $^1$H-NMR (500 MHz, $CDCl_3$): δ 1.12 (3H, t, J=7.63 Hz), 1.59 (3H, s), 1.67 (3H, s), 1.69 (3H, s), 2.06 (1H, quint, J=7.3 Hz), 2.14 (1H, quint, J=7.3 Hz), 2.30 (2H, q, J=7.5 Hz), 2.39 (1H, quint, J=7.1 Hz), 4.04 (2H, d, J=6.9 Hz), 4.72 (1H, s), 4.81 (1H, quint, J=1.6 Hz), 5.05 (1H, tt, J=7.1, 1.5 Hz) ppm.

$^{13}$C-NMR (126 MHz, $CDCl_3$): δ 9.13, 17.76, 19.90, 25.71, 27.61, 28.55, 46.11, 65.61, 112.31, 121.62, 132.85, 144.88, 174.40 ppm.

Mass spectrum: EI (70 eV): m/z 210 ($M^+$), 136, 121, 107, 93, 81, 69, 57, 41, 29

Infrared absorption spectrum (ATR method): ν ($cm^{-1}$) 807, 839, 892, 962, 1020, 1084, 1183, 1272, 1348, 1378, 1451, 1647, 1740, 2917, 2971, 3074.

Example 10: A Process for preparing 2-isopropenyl-5-methyl-4-hexen-1-yl 2-methylbutanoate (6: $R^2$=2-Butyl Group) from 2-isopropenyl-5-methyl-4-hexen-1-ol (5) (this Process Corresponds to the Aforesaid (C) Transesterification with a Carboxylate Ester)

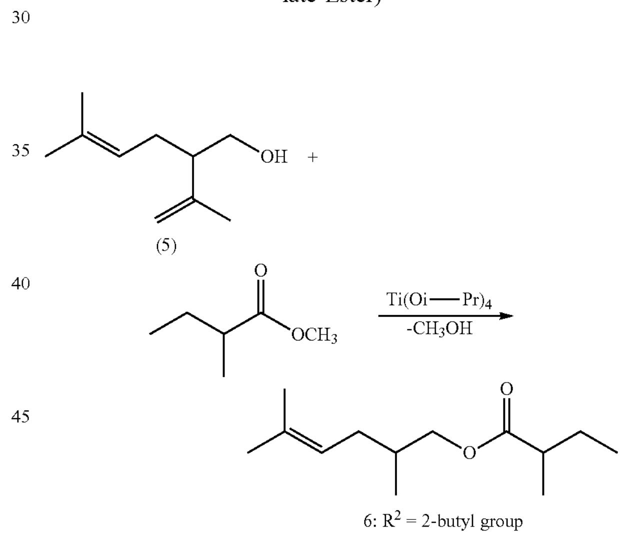

Air in a reactor equipped with a stirrer, a distillation tube, a distillation head, a condenser and a thermometer was purged with a nitrogen gas. Then, to the reactor were placed 2-isopropenyl-5-methyl-4-hexen-1-ol (5) obtained according to Example 6 (154.3 g: 1.0 mol), methyl 2-methylbutanoate (203.3 g: 1.75 mol), and titanium (IV) isopropoxide (2.8 g: 0.01 mol). The mixture was heated to 100° C., while distilling off methanol by-produced with the reaction progress from the top of the distillation head. After the end of distillation of methanol, the pressure in the reactor was gradually reduced to 0.133 KPa, and the temperature in the reactor was raised to 120° C. After excess methyl 2-methylbutanoate was distilled off, the residue was subjected to distillation at a reduced pressure to obtain 2-isopropenyl-5-methyl-4-hexen-1-yl 2-methylbutanoate (6: $R^2$=2-butyl group) (183.7 g: 0.77 mol, yield 77.1%, purity 99.4%).

The following are spectrum data of the 2-isopropenyl-5-methyl-4-hexen-1-yl 2-methylbutanoate (6: $R^2$=2-butyl group) thus prepared.

Nuclear magnetic resonance spectrum: $^1$H-NMR (500 MHz, $CDCl_3$): δ 0.88 (3H, t, J=7.8 Hz), 1.11 (3H, d, J=6.9 Hz), 1.44 (1H, dq, J=7.3, 6.5 Hz), 1.59 (3H, s), 1.61-1.69 (7H, m), 2.06 (1H, quint, J=7.3 Hz), 2.15 (1H, quint, J=7.3, Hz), 2.34 (1H, tq, J=6.9, 6.0), 2.41 (1H, quint, J=7.1 HzHz), 4.01-4.08 (2H, m), 4.73 (1H, s), 4.81 (1H, s), 5.06 (1H, t, J=7.1 Hz) ppm.

$^{13}$C-NMR (126 MHz, $CDCl_3$): δ 11.59, 11.61, 16.63, 17.78, 19.83, 19.85, 25.72, 26.70, 28.58, 41.13, 41.16, 46.20, 65.43, 112.38, 121.66, 132.82, 144.84, 176.63 ppm.

Mass spectrum: EI (70 eV): m/z 238 ($M^+$), 169, 156, 136, 121, 107, 93, 87, 81, 69, 57, 41, 29.

Infrared absorption spectrum (ATR method): ν ($cm^{-1}$) 753, 837, 892, 980, 1014, 1083, 1151, 1182, 1238, 1262, 1355, 1378, 1461, 1647, 1735, 2879, 2935, 2969, 3075.

COMPARATIVE EXAMPLES

The process reported in Patent Literature 1 listed above, in which lithium bis(trimethylsilyl)amide is used as a base to prepare 2-isopropenyl-5-methyl-4-hexenoic acid (4), was carried out as Comparative Examples with various reaction temperatures and various amounts of the base.

Comparative Example 1: Preparation of 2-isopropenyl-5-methyl-4-hexenoic acid (4) Using Lithium Bis(Trimethylsilyl)Amide as the Base

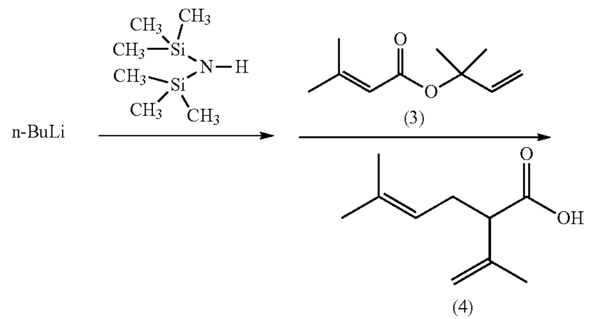

Air in a reactor equipped with a stirrer, a condenser and a thermometer was purged with a nitrogen gas. Then, to the reactor were placed 1,1,1,3,3,3-hexamethyldisilazane (209.8 g: 1.30 mol) and tetrahydrofuran (700.0 g), and the reaction mixture temperature was lowered to 0° C. to 5° C. To the reaction mixture, a solution (727.3 ml) of 1.65 M n-butyllithium (1.20 mol) in n-hexane was added dropwise at a reaction mixture temperature of 5° C. to 10° C. over 1 hour. After the completion of the dropwise addition, the reaction mixture was stirred at a reaction mixture temperature of 25° C. for 1 hour. Then, the reaction mixture temperature was heated to 40° C., and 2-methyl-3-buten-2-yl 3-methyl-2-butenoate (3) (168.2 g: 1.00 mol) was added dropwise at a reaction mixture temperature of 40° C. to 45° C. over 2 hours. After the completion of the dropwise addition, the reaction mixture was stirred at a reaction mixture temperature of 45° C. to 50° C. for 6 hours. The reaction mixture temperature was lowered to 0° C. to 5° C., and an aqueous 10 wt % sodium hydroxide solution (286.0 g) was then added to quench the reaction. The aqueous phase was then separated. To the resulting aqueous phase was added dropwise 20.0 wt % hydrochloric acid (400.0 g) to make the aqueous phase acid. Then, the aqueous phase was subjected to extraction with diethylether (270.0 g). The extract was washed with water (200.0 g) and, then, an aqueous 7.5 wt % sodium chloride solution (200.0 g), and the solvent was then removed at a reduced pressure to obtain 2-isopropenyl-5-methyl-4-hexenoic acid (4) (134.6 g: 0.80 mol, yield 80.9%, purity 80.9%, conversion 98.8%).

The GC results of the obtained product showed that 2-isopropylidene-5-methyl-4-hexenoic acid, which is a regioisomer of 2-isopropenyl-5-methyl-4-hexenoic acid (4), was formed in a production ratio of 8.57%.

Comparative Example 2: Preparation of 2-isopropenyl-5-methyl-4-hexenoic acid (4) Using Lithium Bis(Trimethylsilyl)Amide as a Base

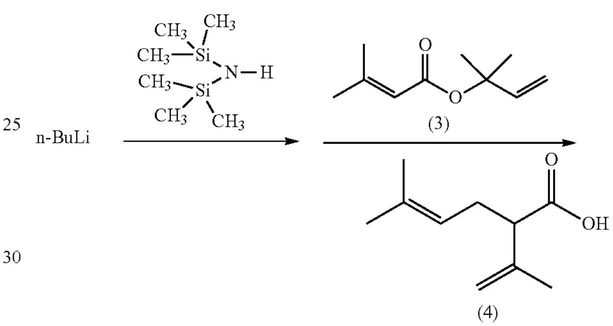

The procedures of Comparative Example 1 were repeated with the exception that the reaction of lithium bis(trimethylsilyl)amide with 2-methyl-3-buten-2-yl 3-methyl-2-butenoate (3) was carried out at 5° C. to 25° C. Obtained was 2-isopropenyl-5-methyl-4-hexenoic acid (4) (149.7 g: 0.83 mol, yield 82.9%, purity 89.1%, conversion 99.1%).

The GC results of the obtained product showed that 2-isopropylidene-5-methyl-4-hexenoic acid, which is a regioisomer of 2-isopropenyl-5-methyl-4-hexenoic acid (4), was formed in a production ratio of 1.10%.

Comparative Example 3: Preparation of 2-isopropenyl-5-methyl-4-hexenoic acid (4) Using Lithium Bis(Trimethylsilyl)Amide as a Base

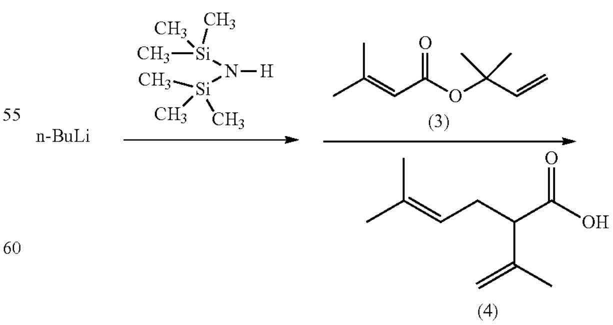

The procedures of Comparative Example 1 were repeated with the exception that 1,1,1,3,3,3-hexamethyldisilazane (171.1 g: 1.06 mol) and a solution (618.2 ml) of 1.65 M n-butyllithium (1.02 mol) in n-hexane were used. Obtained was 2-isopropenyl-5-methyl-4-hexenoic acid (4) (117.8 g: 0.70 mol, yield 70.3%, purity 82.5%, conversion 77.8%).

The GC results of the obtained product showed that 2-isopropylidene-5-methyl-4-hexenoic acid, which is a regioisomer of 2-isopropenyl-5-methyl-4-hexenoic acid (4), was formed in a production ratio of 1.83%.

The invention claimed is:

1. A process for preparing 2-isopropenyl-5-methyl-4-hexenoic acid of the following formula (4):

(4)

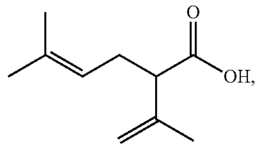

the process comprising steps of:

subjecting a Grignard reagent of the following general formula (1):

$$R^1MgX \quad (1)$$

wherein $R^1$ represents a linear, branched, or aromatic monovalent hydrocarbon group having 1 to 8 carbon atoms, and X represents a chlorine atom, a bromine atom, or an iodine atom, and 1,1,1,3,3,3-hexamethyldisilazane to a deprotonation reaction to form a 1,1,1,3,3,3-hexamethyldisilazane derivative; and subjecting 2-methyl-3-buten-2-yl 3-methyl-2-butenoate of the following formula (3):

(3)

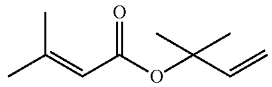

to a rearrangement reaction in the presence of the 1,1,1,3,3,3-hexamethyldisilazane derivative to form 2-isopropenyl-5-methyl-4-hexenoic acid (4).

2. A process for preparing 2-isopropenyl-5-methyl-4-hexen-1-ol of the following formula (5):

(5)

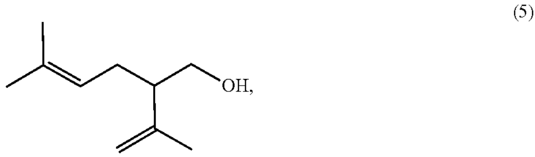

the process comprising steps of:

the process according to claim 1 for preparing 2-isopropenyl-5-methyl-4-hexenoic acid (4), and reducing the 2-isopropenyl-5-methyl-4-hexenoic acid (4) thus prepared to form 2-isopropenyl-5-methyl-4-hexen-1-ol (5).

3. A process for preparing a 2-isopropenyl-5-methyl-4-hexen-1-yl carboxylate of the following general formula (6):

(6)

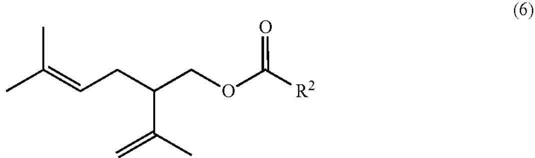

wherein $R^2$ represents a linear or branched monovalent hydrocarbon group having 1 to 6 carbon atoms, the process comprising steps of:

the process according to claim 2 for preparing 2-isopropenyl-5-methyl-4-hexen-1-ol (5), and esterifying the 2-isopropenyl-5-methyl-4-hexen-1-ol (5) thus prepared to form 2-isopropenyl-5-methyl-4-hexen-1-yl carboxylate (6).

* * * * *